US011619524B2

(12) United States Patent
Moore

(10) Patent No.: US 11,619,524 B2
(45) Date of Patent: Apr. 4, 2023

(54) DENTAL EQUIPMENT MONITORING SYSTEM

(71) Applicant: Brandon Moore, Gainesville, VA (US)

(72) Inventor: Brandon Moore, Gainesville, VA (US)

(*) Notice: Subject to any disclaimer, the term of this patent is extended or adjusted under 35 U.S.C. 154(b) by 622 days.

(21) Appl. No.: 16/460,365

(22) Filed: Jul. 2, 2019

(65) Prior Publication Data
US 2020/0011713 A1 Jan. 9, 2020

Related U.S. Application Data

(60) Provisional application No. 62/693,828, filed on Jul. 3, 2018.

(51) Int. Cl.
G08B 23/00 (2006.01)
G01D 7/08 (2006.01)
A61C 17/02 (2006.01)
A61C 17/022 (2006.01)
G01D 7/00 (2006.01)
A61G 15/00 (2006.01)
A61B 1/24 (2006.01)
G01D 21/02 (2006.01)
A61C 17/06 (2006.01)
(Continued)

(52) U.S. Cl.
CPC ................ G01D 7/08 (2013.01); A61B 1/24 (2013.01); A61C 17/02 (2013.01); A61C 17/022 (2013.01); A61C 17/06 (2019.05); A61G 15/00 (2013.01); G01D 7/005 (2013.01); G01D 21/02 (2013.01); G16H 40/63 (2018.01); A61G 2203/30 (2013.01); A61M 16/0051 (2013.01)

(58) Field of Classification Search
CPC .......... G01D 7/08; G01D 7/005; G01D 21/02; A61B 1/24; A61C 17/02; A61C 17/022; A61C 17/06; A61G 15/00; A61G 2203/30; G16H 40/63
USPC ........................................................ 340/500
See application file for complete search history.

(56) References Cited

U.S. PATENT DOCUMENTS 6,470,222 B1 10/2002 Davidson et al.
7,752,012 B2 7/2010 Kavaklioglu
7,768,414 B2 8/2010 Abel et al.
(Continued)

FOREIGN PATENT DOCUMENTS

CN 102819253 B 3/2015
DE 10139020 A1 3/2003
(Continued)

Primary Examiner — Tai T Nguyen
(74) Attorney, Agent, or Firm — Jonathan Brown

(57) ABSTRACT

A non-invasive dental or surgical monitoring system is disclosed. The monitoring system is comprised generally of dental or surgical equipment to be monitored, a main sensor unit, a set of sensors. The main sensor unit is in communication with various sensors removably attached to the equipment. The sensors monitor environment conditions related to the equipment rather than directly monitoring the equipment. The collected data is sent to the main sensor unit and can be accessed, or wirelessly transmitted by signal to a device or devices at another location. As collected data aggregates, a data profile can be created, machine learning can be used to discover patterns, and predictive analysis can be incorporated to help software make predictions of, or spot in real time, equipment problems based on deviations from the profile.

17 Claims, 12 Drawing Sheets

(51) Int. Cl.
    *G16H 40/63*     (2018.01)
    *A61M 16/00*     (2006.01)

(56) References Cited

U.S. PATENT DOCUMENTS

| | | |
|---|---|---|
| 7,966,269 B2 | 6/2011 | Bauer et al. |
| 8,190,543 B2 | 5/2012 | Kaushal et al. |
| 8,566,115 B2 | 10/2013 | Moore |
| 2005/0058962 A1* | 3/2005 | Siemons ................ A61C 19/00 433/27 |
| 2006/0290525 A1 | 12/2006 | Andersen et al. |
| 2011/0316691 A1 | 12/2011 | Pepin et al. |
| 2018/0052454 A1* | 2/2018 | Magno ................ A61C 1/0007 |
| 2019/0104919 A1* | 4/2019 | Shelton, IV ........... A61B 34/25 |

FOREIGN PATENT DOCUMENTS

| | | |
|---|---|---|
| EP | 0766949 A2 | 4/1997 |
| WO | WO 2016174187 A1 | 11/2016 |

\* cited by examiner

DENTAL EQUIPMENT MONITORING SYSTEM

CROSS REFERENCE TO RELATED APPLICATION(S)

This application claims the benefit of, U.S. Provisional Patent Application No. 62/693,828, entitled "DENTAL EQUIPMENT MONITORING SYSTEM," filed on Jul. 3, 2018, the subject matter of which are hereby incorporated therein by reference in their entirety.

TECHNICAL FIELD OF THE INVENTION

The present invention relates to the general art of dental equipment monitoring, and more specifically to an apparatus for effective and passive monitoring of dental or surgical facilities.

BACKGROUND OF THE INVENTION

Dental practices have a good deal of electrical and mechanical equipment that they operate for completing various dental procedures on patients. Two critical pieces of equipment in a typical dental practice, as examples, are one or more vacuum pumps, and at least one compressor. The vacuum pump provides chair-side suction for purposes such as clearing away debris from a patient's mouth during cleanings, root canals, bridge work, surgery and other dental procedures and the compressor drives the instruments used to perform procedures. If either of those two pieces of equipment were to become inoperable, the practice would immediately start losing money in the form of lost production.

Dental practices tend to have crowded schedules and can be booked by patients up to several months in advance. Accordingly, it is important that dental equipment function as close to 100% of the time as possible. When a piece of equipment breaks down, any amount of time that equipment is down, since a dental practice is likely to be heavily booked, is very likely to be costly in terms of patient appointments that have to be canceled or postponed. This also results in increased inconvenience, or in some cases suffering, by patients that have their appointments canceled or postponed.

In addition, equipment repair of replacement after a piece equipment has broken down can be expensive, and generally, repair or replacement costs are much higher after a piece of equipment has failed than when effective maintenance, repair and component replacement in advance prevents failure.

A maintenance method currently employed is for technicians to conduct routine visual inspections of dental practice equipment to ascertain equipment status. While such inspections can routinely and identify some problems visible to the human eye, these are limited to items that can be spotted visually, such as leaking lines or corroding parts. Typically, when a piece of equipment breaks down, the dental practice has to contact an equipment technician to come inspect the equipment in person, determine what is wrong, and either repair or replace the equipment, or send it to a shop for the same. In either case, much time can be lost while the practice does not have the equipment and awaits its return to working order. Needless to say, if equipment problems can be spotted and dealt with in advance, typically when the practice is closed, rather than in a reactive manner after the equipment has broken, this can save a lot of lost time and cost.

Another method for checking dental practice equipment is the integration of sensor components into the manufactured products, including medical equipment, with specific and remote monitoring of each such product. At least one manufacturer "baked in" sensors into its products and provides monitoring of these sensors. Collection of equipment data over a period of time is also known. For example, patent WO 2016174187 A1 discloses the collection of data over a number of equipment cycles and the use of that collective information, with the issuance of an alert if a piece of equipment falls outside a set of parameters.

However, active monitoring of specific pieces of equipment presents a number of obstacles to smooth overall functioning of an overall system. When the manufacturer of an item builds in a sensor into its own equipment, it is likely that monitoring would have to be arranged through the manufacturer, or through a party with monitoring equipment compatible with that of the manufacturer. Typically, a dental practice will have equipment by more than one manufacturer, resulting in a situation in which monitoring systems of the equipment may not be compatible with, or at the least not work effectively with, each other. This could result in s system with multiple separate monitoring set-ups for the equipment in s single practice. Further, some equipment may not have built-in manufacturer sensor components, resulting in a situation in which some equipment can be remotely monitored and some cannot.

Another possibility is altering pieces of equipment by building in sensor components. However, altering equipment to add sensors or monitoring can damage or destroy the equipment. Typically, damage of equipment is not covered by any warrantees or manufacturer guarantees, which creates a great natural reluctance to make such alterations.

Accordingly, even when some level of equipment monitoring is created, it tends to focus on some individual components, rather than provide uniform monitoring of the entire system. This results in a system wherein some pieces of equipment have better monitoring than others, independent of actual relative importance of likelihood of failure of the individual system components. This results in a practice system with a lack of cohesion or focus. The unanticipated breakdown of a piece of less monitored equipment is typically as likely to result in the problems noted herein as the breakdown of a more monitored piece.

Additionally, operating conditions can vary somewhat from one dental practice to another, such that a condition that is completely normal at one practice may be outside the norm at another practice and be an indicator of trouble. For example, even though they are both indoors, the ambient conditions equipment operate in are likely to be somewhat different between two respective practices in Fairbanks Ak. and Tallahassee Fla., so these are likely to have different maintenance needs. A level of humidity that may be normal in the Tallahassee practice may be a concerning indicator in the Fairbanks practice. Even power measurements may be different at respective practices. For example, the power grid in Tallahassee may run a lower voltage as more people are operating air conditioners during the summer compared to the power grid in Fairbanks, which has cooler weather during the summer.

Also, conditions may change within the same practice over the course of a year, such that a temperature in the Fairbanks practice that may be perfectly normal in June may be elevated and concerning in January.

In addition, similar issues of monitoring can also occur in a surgical practice or setting.

Two promising technologies that have recently emerged in society are machine learning and predictive analysis. Machine learning is a type of artificial intelligence (AI) that provides computers with the ability to learn without being explicitly programmed. Machine learning, through the use of algorithms, focuses on the development of computer programs that can change when exposed to new data.

By contrast, a system known as "data mining" extracts data for discovery of patterns within the data that may be acted upon but relies upon human comprehension and analysis to do so. Machine learning uses software itself to discover patterns within data, and can self-adjust a program or actions accordingly.

A popular example of emerging machine learning is Facebook's News Feed, wherein machine learning, through pre-created algorithms, are used to discern user preferences and pattern of behavior, such as what posts a user "likes" or articles a user chooses to read, to adjust and personalize each member's feed. If a member frequently stops to read or "like" a particular friend's posts, machine learning will notice this pattern and the News Feed will start to show more of that friend's activity earlier in the feed. These patterns are identified using predictive analysis.

Predictive analysis is a methodology used in data mining and machine learning, wherein statistical patterns emerging from data are used to predict likely possible future behavior. For example, if many consumers typically enter a pattern of behavior (e.g., using cards to their limits, taking out additional cards, moving to minimum payments, etc.) before defaulting on a credit card, predictive analysis could be used, based on statistical analysis of such patterns compared to default rates, to make default predictions about a specific consumer. If this is incorporated into an algorithm, such that a computer could incorporate this and increasing amounts of comparative data to make increasingly accurate real time individual predictions, this would be a type of "machine learning."

What is needed is a system and method that addresses these monitoring issue, providing a non-invasive, efficient method for monitoring dental facilities.

SUMMARY

A non-invasive dental or surgical monitoring system ("dental monitoring system") is disclosed. The dental monitoring system is comprised generally of a main sensing unit, a set or sets of sensors, dental apparatus, and appropriate lines to be monitored.

A main sensor unit ("main unit") is provided. The main sensor is in communication with various portions of apparatus in use throughout the dental practice area. In one embodiment, these are represented as a pair of sample typical apparatus; a vacuum pump and a compressor, though apparatus can be added or removed. These and other dental apparatus, particularly other apparatus that makes use of air or water, can also be monitored.

In this embodiment, as water enters the vacuum pump via the water line and flow meter, a set of sensors monitor suitable characteristics of the equipment environment, such as, e.g., sound, moisture level, temperature, and/or air pressure and transmitted via suitable means to the main unit. The sensors, by monitoring environmental conditions, do not directly monitor the equipment. They are not directly attached to or combined with the equipment, such as vacuum pump or compressor. The sensors typically monitor data regarding conditions such as environment, moisture, pressure, electrical current (e.g., decreased voltage leading to too much amperage) sounds (changes in 'hums' or other equipment noise) and the like. Because the sensors are monitoring conditions rather than the equipment itself, the dental monitoring system is "witnessing" or "observing" the equipment operation in a passive manner. The sensor Array has no control or interaction over the operation of the equipment. The sensors do not interfere with the operation of the equipment and should any fail, have no impact on the equipment's operation.

The non-invasive operation of the sensors provides a number of important advantages. It prevents possible damage or malfunction to the equipment that might result from alteration, and helps prevent the voiding of any warrantees that can happen when equipment is altered. It also renders replacement of any of the equipment or sensors much easier. This data is collected and transmitted to the main unit. Additionally, data from the flow meter can also be transmitted to the main unit.

The main unit collects the incoming information from the sensors via a local processor provided within the main unit. The data may be collected within the main unit and accessed as necessary, or the data can be wirelessly transmitted by signal to a device or devices at another location.

The main unit can be further comprised of a touch screen or other known display so that a user can directly access and read the collected data. Alternatively, the main unit can transmit the collected data to known electronic means, such as, e.g., a PC or laptop computer, smart phone or tablet, in or near the practice at a local location, or even to a remote location.

Similar collection and processing of data is also shown in another piece of sample equipment. A compressor is provided. A set of sensors is provided and monitors conditions about the compressor and related apparatus. An air line(s) leading from the compressor can pass through an air sensor box, having detection apparatus. As with the sensors about the vacuum pump, the sensors collect data and in this embodiment, the data is transmitted via a set of wires to the main sensor.

Additionally, a suitable number of room sensors may be deployed about the room to assist in profiling and monitoring general environmental conditions of the room(s) the equipment is in.

In addition, a set of RPM sensors can be deployed to monitor the operating speed of any motors in the system such as the motor of the vacuum pump or compressor. The RPM sensors can transmit RPM data to the main sensor or other suitable location, so that if there are significant changes in RPM, which can indicate upcoming mechanical problems, this can be noted and the motor checked immediately.

A number of types of sensors can be deployed, depending on which data is required for effective monitoring of the dental monitoring system. Types of sensors that can be deployed within this array are those suitable for non-invasively monitoring conditions as discussed.

In addition to a wide assortment of sensor data, a wide assortment of non-sensor data that can have an impact within a practice or mechanical room may also be collected as part of the baseline and continuing set of profile data to improve the accuracy of the profile. For example, weather data can be pulled from a variety of Internet based feeds, and used in computation of practice conditions such as humidity and temperature, as well as variation of such data throughout the year which can result in differing baseline conditions of these factors at different times.

The non-invasive data regarding environmental and other conditions is monitored, collected and processed for a suitably long period. Monitoring can be constant, but is often conducted at specified intervals to gather sufficient data without overuse and excessive wear of the monitoring apparatus. Each dental practice or area will have its own specific set of conditions based on factors such as what equipment is in the practice, where the practice is located, and time of day. A profile of sensor data can be eventually collected of that individual dental practice and/or mechanical room, such as that practice or mechanical room's normal range of temperature, air pressure, noise level, moisture, to create an individualized profile for a specific dental monitoring system, with a resulting customized profile or "fingerprint" of condition data to the specific dental practice.

The results from these initial monitoring sessions will help set a baseline behavior pattern, to assist with determining if the equipment is operating out of specified ranges specific to that room. For example, a compressor in Colorado might take longer to charge up than a Compressor in Virginia due to changes in elevation. A Vacuum in Alaska may run cooler than a Vacuum in Texas on a summer day.

As the data for a profile from the sensors increases, machine learning can be used to discover patterns. These patterns can include patterns of monitored data ranges of the sensors with equipment is functioning normally, and patterns of sensor data changes as they relate to general problems or specific equipment issues. Predictive analysis can be incorporated to help software make predictions of, or spot in real time, equipment problems based on deviations from the profile. Over time, as more and more pattern data is collected, the profile will grow stronger, and predictions based upon the profile increase in accuracy.

As an example, if a piece of equipment repeatedly experiences a rise in temperature a specific amount of time before an electrical shutdown or electrical-related damage, machine learning would note this deviation from the profile and its results, and predictive analysis could be used to analyze this and show the probability of a future breakdown based on the temperature of that piece of equipment at a given time. If the temperature rises, the system could then predict a likely impending electrical failure. The party maintaining that piece of equipment can be alerted in advance, and the equipment replaced at convenience before a shutdown or damage occurs. Action can be proactive, with little or no time loss, rather than reactive.

The means of transmitting data from the various sensors to the main unit or other appropriate processors can be any suitable in the art. In an embodiment, the data is sent via the set of wires, but can be wireless as well.

The combined actions of these sensors, along with universal monitoring and use of machine learning by the main unit processor, work together to create a sensor array that is "tripped" when one or more monitored conditions fall outside that sensor array.

The air sensor box encapsulates sensor apparatus for monitoring the air line and detecting any noticeable changes that can indicate problems. A pressure gauge monitors the pressure within the line and if the pressure changes, raising or lowering, outside the profile, this information can be transmitted to the main unit.

Next to the pressure gauge is apparatus for monitoring the moisture within the air line and if the moisture moves past an allowable limit set in the profile, this information can likewise be transmitted to the main unit. In this specific embodiment, the moisture apparatus is comprised of a repressive moisture indicator, also known as a liquid contact indicator, and a Red and Blue, or Red, Green and Blue color (RGB)/LED sensor set with LED light.

The RGB sensor portion of the RGB/LED Sensor set is a relatively simple sensor designed and provided to detect a color change from blue to red or pink. The RGB sensor is capable of providing a read out of the color of a specific object in front of it. For example, and in this embodiment, the RGB/LED sensor can be placed in front of a repressive moisture indicator. Any deviation in color beyond the range that the RGB sensor is set to recognize as "good" color will be detected and result in alarm being sent by the system. The LED light on the sensor is to illuminate the indicator.

For example, if there is a leak that raises moisture and the repressive moisture indicator turns red, the RGB sensor detects the change in color and is programmed such that the attached LED light, preferably a red light, turns on, when the color change occurs. The LED light sensor portion reads the activation of the LED light and this information is transmitted to the main unit, or elsewhere as appropriate, by wired or wireless means.

In another embodiment, if one or more aspects of the incoming non-invasive sensor data move outside the specific dental monitoring system profile, such as, e.g., an abnormally raised sound level of the equipment, vibration, or increased moisture content, the main unit can recognize this and transmit a general or more descriptive alert, depending upon what it is programmed to do, via means known in the art. Routine data, at specified intervals, can also be transmitted.

For example, the data or alert can be sent to another local device such as, e.g., a practice PC or laptop that the main unit is directly connected to, or it can be sent, as in this embodiment, as a signal via a modem to the local electronic device.

The main unit can, alternatively, be fitted with software and components such that it can transmit to a remote electronic device. For example, the unit microprocessor can be capable of accessing the internet and sending data to a server or cloud, to be forwarded to appropriate personnel. The main unit may also be fitted with software and components making it capable of sending routine data or an alert to a mobile device or devices such as a smart phone or tablet, such that anyone that should be notified can be notified in real or nearly real time. The local device or remote device can also be provided with the capability of forwarding data or alerts to the mobile devices.

In an alternative embodiment, the non-invasive dental monitoring system can be used with a dual stage, or dual head, compression system with single or more compressors. The compressor(s) and heads are monitored by the system via sensors fitted about the compressor. Data input is collected by a wireless signaling device, which in turn transmits wireless signals to the main unit. The signals are transmitted to the main unit and processed as other received data from the sensors.

In another alternative embodiment, the compressor can be a single head type with a single vacuum pump. In this embodiment, the vacuum pump is a wet ring vacuum pump: a vacuum pump in which an operating liquid is put into motion, often by an impeller, and accelerated, forming a liquid ring.

In another alternative embodiment, the compressor is a dual head compressor and a single vacuum pump. The vacuum pump can be of any suitable type, such as a regular pump, a wet ring vacuum pump or as in this embodiment, a two-state pump.

In another alternative embodiment, the compressor is a triple head compressor, with a triple set of compressor sensors and the vacuum pump is a dual pump dry type vacuum.

In another alternative embodiment, the compressor is a single head compressor and the vacuum pump is with single pump dry vacuum In another alternative embodiment, the equipment to be monitored is a compressor, and the compressor is a dual head compressor. Also in this embodiment, the sensors are sending data to a remote display at the portable electronic device via the main sensor unit so that the compressor can be monitored from any location.

Hereby disclosed is a device for non-invasive dental facility monitoring.

DETAILED DESCRIPTION OF PREFERRED EMBODIMENTS

Other objects, features and advantages of the invention will become apparent from a consideration of the following detailed description and the accompanying drawings. The following descriptions are made referring to the figures, wherein like reference numbers refer to like features throughout this description. Not all numbers appearing in one figure are necessarily present in another.

Figure 1:
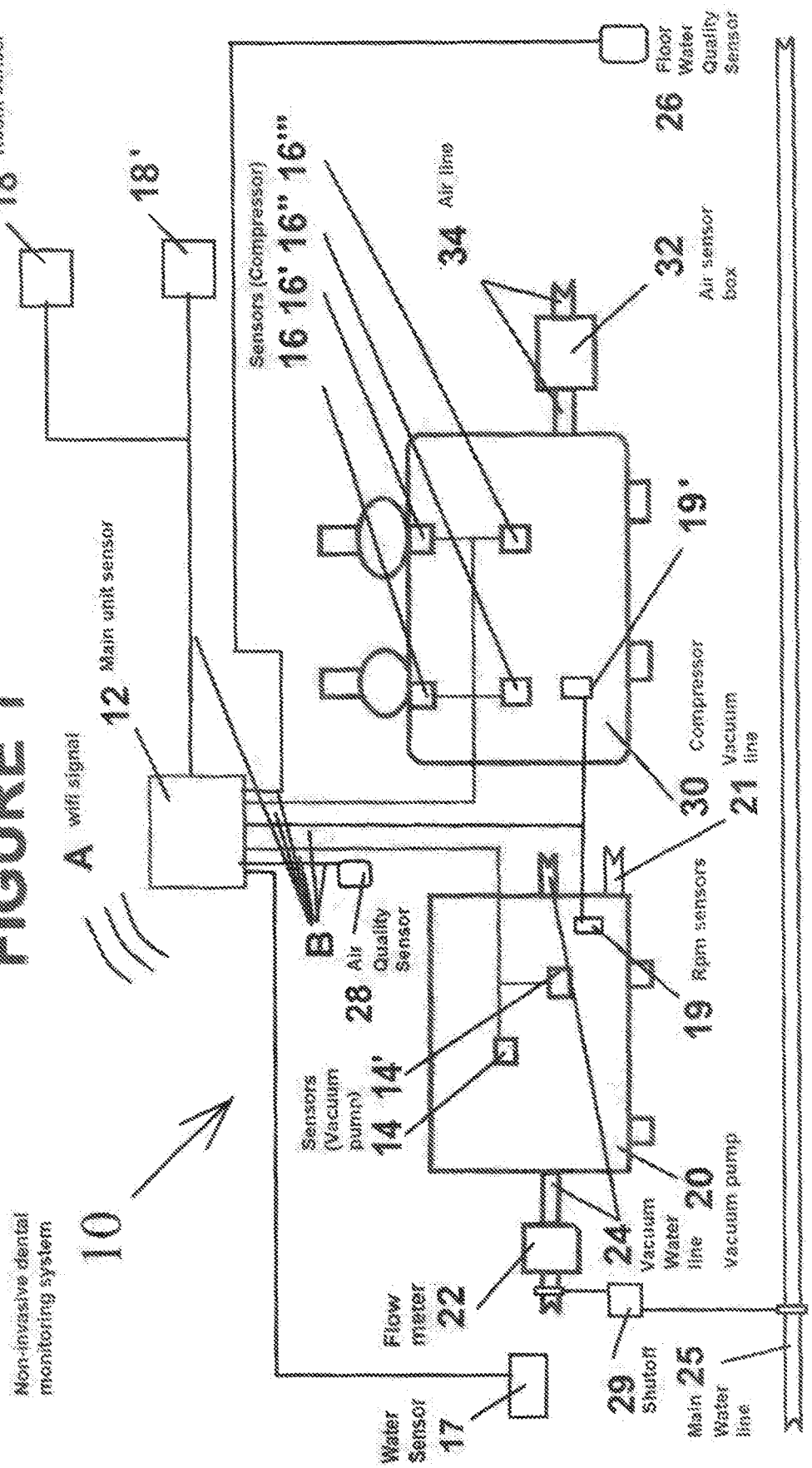
FIG. 1 is a schematic side view of a preferred embodiment of the invention.

Turning first to FIG. 1, a non-invasive dental or surgical monitoring system 10 ("dental monitoring system") is shown and featured. The dental monitoring system 10 is comprised generally of a main sensing unit 12, a set or sets of sensors (represented here as 14-14' and 16-16''') dental apparatus (represented here as 20, 30) and appropriate lines (represented here as 24, 34) to be monitored. The monitoring system 10 and equipment can be located in any suitable location or locations. The equipment it is noted that often, as in this embodiment, the dental apparatus 20, 30, is placed in a distinct and dedicated "mechanical room" or "utility room" so much or all of the monitoring system 10 is placed there of necessity as well. The dental apparatus 20, 30 or monitoring system can be further placed in other suitable locations, such as, for example, a cabinet within a patient room or other room, or be divided among two or more rooms or areas of rooms, depending upon circumstances.

A main sensor unit 12 ("main unit") is provided. The main sensor 12 is in communication with various portions of apparatus in use throughout the dental practice area. In this embodiment, these are represented as a pair of sample typical apparatus; a vacuum pump 20 and a compressor 30. These are representative and there can be provided, as necessary, more vacuum pumps and/or compressors, and other dental apparatus that makes use of air or water as known in the art, and could also be monitored.

The dental equipment in this embodiment is comprised of at least two types of water lines. A first, main water line 25 provides water for dental treatment. This is, for example, the water in a sink, or in a water pick, or water used to drain material from a patient's mouth during procedures.

Vacuum pumps can, generally, be dry pumps or wet pumps. Dry pumps do not need water to operate. Wet pumps have some superior characteristics, but need an amount of water to operate. In this embodiment, a wet pump is shown. The vacuum pump 20, accordingly, has a vacuum water line 24 to provide water to the pump 20 or associated equipment. A vacuum line 21 leaves the pump to provide a vacuum as needed to dental equipment in a treatment area.

As water enters the vacuum pump 20 via the water line 24 and flow meter 22, a set of sensors 14, 14' monitor suitable characteristics of the equipment environment, such as, e.g., sound, moisture level, temperature, and/or air pressure and transmitted via suitable means to the main unit 12. The sensors 14, 14', by monitoring environmental conditions, do not directly monitor the equipment. They are not directly attached to or combined with the equipment, such as vacuum pump 20 or compressor 30. The sensors typically monitor data regarding conditions such as environment, moisture, pressure, electrical current (e.g., decreased voltage leading to too much amperage) sounds (changes in 'hums' or other equipment noise) and the like. Because the sensors are monitoring conditions rather than the equipment itself, the dental monitoring system 10 is "witnessing" or "observing" the equipment operation in a passive manner. The sensor Array has no control or interaction over the operation of the equipment. The sensors do not interfere with the operation of the equipment and should any fail, have no impact on the equipment's operation.

The non-invasive operation of the sensors provides a number of important advantages. It prevents possible damage or malfunction to the equipment that might result from alteration, and helps prevent the voiding of any warrantees that can happen when equipment is altered. It also renders replacement of any of the equipment or sensors much easier. This data is collected and transmitted to the main unit 12. Additionally, data from the flow meter 22 can also be transmitted to the main unit 12.

The main unit 12 collects the incoming information from the sensors 14, 14' via a local processor provided within the main unit 12. The data may be collected within the main unit 12 and accessed as necessary, or the data can be wirelessly transmitted by signal to a device or devices at another location, represented here as.

The main unit 12 can be further comprised of a touch screen or other known display so that a user can directly access and read the collected data. Alternatively, the main unit 12 can transmit the collected data to known electronic means, such as, e.g., a PC or laptop computer, smart phone or tablet, in or near the practice at a local location, or even to a remote location.

Similar collection and processing of data is also shown in another piece of sample equipment. A compressor 30 is provided. A set of sensors 16, 16',16",16'", is provided and monitors conditions about the compressor 30 and related apparatus. An air line(s) 34 leading from the compressor 30 can pass through an air sensor box 32, having detection apparatus. As with the sensors about the vacuum pump 20, the sensors 16, 16',16",16'", collect data and in this embodiment, the data is transmitted via a set of wires, represented herein as "B", to the main sensor.

One or more water sensor(s) 17 can be provided and situated so as to detect sudden onset of moisture such as leaks. A water sensor 17 can, for example, be placed on the floor of equipment room as herein and or in the chassis of any wet-ring type vacuums.

Additionally, a suitable number of room sensors, depicted as 18, 18' may be deployed about the room to assist in profiling and monitoring general environmental conditions of the room(s) the equipment is in.

In addition, a set of RPM sensors 19, 19' can be deployed to monitor the operating speed of any motors in the system such as the motor of the vacuum pump 20 or compressor 30. The RPM sensors can transmit RPM data to the main sensor 12 or other suitable location, so that if there are significant changes in RPM, which can indicate upcoming mechanical problems, this can be noted and the motor checked immediately.

Further, one or more floor water sensor(s) (represented herein as 26) can be added to alert of unexpected moisture or wet conditions on the floor. The floor water sensor 26 can, depending upon conditions, be set to warn when it is placed in contact with a level of moisture, or any moisture at all. Typically, the floor water sensor 26 will be located in the utility room or other location of the dental apparatus 20, 30. The floor water sensor, like other sensors, can be adjusted to expected local conditions of moisture in the area. For example, a small amount of detected moisture could be more indicative of a problem in New Mexico in January than in Florida in July.

In any case, the floor water sensor can be particularly useful in two situations. First, if there is flooding or leaking of the area, resulting in moisture accumulation on the floor because of an environmental flood, plumbing problem or other typical reason, the floor water sensor 26 can alert the dental office or appropriate technician to the problem before more serious damage ensues. Second, if there is moisture accumulation because of moisture leaking from any of the equipment, the moisture will likely pool to the floor. The floor water sensor 26 can then detect and report on the moisture, alerting appropriate parties to the problem so repairs can be made.

In addition, one or more air quality sensor(s) (represented herein as 28) can be placed about the room or area of the equipment. The air quality sensor 28 can be of the type (or programmed) to detect a general change in air quality, or an increase or decrease in a specified gas. Such changes can indicate a leak of gas from a piece of equipment or other problem, such as a failing piece of equipment. An air quality sensor 28 designed to detect increasing carbon dioxide, carbon monoxide, or other components of smoke can also detect a general fire, or overheating of a piece of equipment.

A number of types of sensors can be deployed, depending on which data is required for effective monitoring of the dental monitoring system 10. Types of sensors that can be deployed within this array are those known in the art and suitable for non-invasively monitoring conditions as discussed.

Some examples of these types of sensors can include:
Current Transformer(s) for measuring current flowing to electric motors for detecting power spikes or drops,
Humidity sensor(s) for measuring ambient humidity,
Temperature sensor(s) for measuring ambient air temperature. Further, if a temperature sensor is affixed to the housing of a motor, the temperature of motor(s) can be measured and reported to provide an indirect reading on the state of the motor(s),
Vibration sensors on motors to detect the changes in balance and vibration of various pieces of equipment such as pumps or motors, sound sensor(s) (e.g., microphone(s)) for collecting sound data "listening" of the room generally, and/or targeted sound sensor(s) for collecting sound data of specific pieces of dental practice equipment,
Air quality detector(s) to detect levels of various harmful substances in the air and/or substances that rise when equipment problems are more likely to come or are happening,
Air Pressure sensor(s) to detect both air tank pressure and/or purge air pressure (a specific pressure measurement related to dental compressors with air dryers),
Water sensor(s) capable of detecting changes in the presence or absence of water to detect increased conditions of dryness or moisture, particularly floods or overflows,
Water flow sensor(s), installed at water lines rather than within pieces of equipment, for monitoring the rate of water flow within a water line to detect water flow to vacuum pumps, and vacuum sensors to assist with detecting blocked vacuum lines throughout the practice.

In addition to a wide assortment of sensor data, a wide assortment of non-sensor data that can have an impact within a practice or mechanical room may also be collected as part of the baseline and continuing set of profile data to improve the accuracy of the profile. For example, weather data can be pulled from a variety of Internet based feeds, and used in computation of practice conditions such as humidity and temperature, as well as variation of such data throughout the year which can result in differing baseline conditions of these factors at different times.

The non-invasive data regarding environmental and other conditions is monitored, collected and processed for a suitably long period. Monitoring can be constant, but is often conducted at specified intervals to gather sufficient data without overuse and excessive wear of the monitoring apparatus. Each dental practice or area will have its own specific set of conditions based on factors such as what equipment is in the practice, where the practice is located, and time of day. A profile of sensor data can be eventually collected of that individual dental practice and/or mechanical room, such as that practice or mechanical room's normal range of temperature, air pressure: noise level, moisture, to create an individualized profile for a specific dental monitoring system 10, with a resulting customized profile or "fingerprint" of condition data to the specific dental practice.

The results from these initial monitoring sessions will help set a baseline behavior pattern, to assist with determining if the equipment 20, 30 is operating out of specified ranges specific to that room. For example, a compressor in Colorado might take longer to charge up than a Compressor in Virginia due to changes in elevation A Vacuum in Alaska may run cooler than a Vacuum in Texas on a summer day.

It is noted that the equipment is often located within a 'mechanical room' or "utility room" within the dental practice and sensors may be placed to record and monitor data primarily or completely within this room. As part of the installation, sensor installers, such as technicians, will need to confirm that the equipment and sensors, such as, e.g., the dryer system, are in good working order to insure accuracy of the initial "system normal" profile.

Returning to the representative sensors 14, 14',16-16''', 18-18', as the data for a profile from the sensors 14, 14',16-16''', 18-18', increases, machine learning can be used to discover patterns. These patterns can include patterns of monitored data ranges of the sensors with equipment is functioning normally, and patterns of sensor data changes as they relate to general problems or specific equipment issues. Predictive analysis can be incorporated to help software make predictions of, or spot in real time, equipment problems based on deviations from the profile. Over time, as more and more pattern data is collected, the profile will grow stronger, and predictions based upon the profile increase in accuracy.

As an example, if a piece of equipment repeatedly experiences a rise in temperature a specific amount of time before an electrical shutdown or electrical-related damage, machine learning would note this deviation from the profile and its results, and predictive analysis could be used to analyze this and show the probability of a future breakdown based on the temperature of that piece of equipment at a given time. If the temperature rises, the system could then predict a likely impending electrical failure. The party maintaining that piece of equipment can be alerted in advance, and the equipment replaced at convenience before a shutdown or damage occurs. Action can be proactive, with little or no time loss, rather than reactive.

Additionally, if data is available for more than one dental practice, for example when there is a network of connected practices, data produced from monitoring of a piece of equipment in one dental practice can also be compared and aggregated with other similar pieces equipment pieces in other dental practices to determine an average or standard signature for a piece of equipment across the entire network of devices. With this increased data, the profile can be refined and improved further.

Also, because an individual profile is developed for each dental practice this can address the issue of different profile and maintenance conditions resulting from changing conditions between different practices and across different times of the year.

The means of transmitting data from the various sensors to the main unit or other appropriate processors can be any suitable in the art. These remote sensors 14, 14',16-16''', 18-18', for example, may be connected via attached wired hardwire that send data from respective sensors, or using wireless technology as known in the art. Examples of wireless technology include, for example, 802.11 or Mesh network capabilities. In this embodiment, the data is sent via a set of wires "B." Advantages of a wired network can include increased reliability and a steady power supply to the sensors 14, 14',16-16''', 18-18'.

The combined actions of these sensors, along with universal monitoring and use of machine learning by the main unit 12 processor, work together to create a sensor array that is "tripped" when one or more monitored conditions fall outside that sensor array.

A shutoff 29, capable of immediately turning off portions or all of the equipment, can be provided. In large part, the concern raised by dental offices is that of flooding because of the use of flowing water. Accordingly, the shutoff 29, as in this embodiment, can be designed to shut off the water lines 24, 25. In addition, the shutoff 29 can be further designed to immediately cut power to all components, shut off components, or take other immediate action upon command to prevent damage. The shutoff can be used daily, and can be manual or tied to the system, and turned off via machine command.

Further, the shutoff can additionally be designed to be activated remotely, or even automatically by the system, when certain emergency parameters are met. For example, if a signal is sent from the floor water sensor 26 to the main sensor unit 12 indicating a leak or flooding, the monitoring system can send this as an alert to pre-determined parties, or it can automatically use the shutoff. In this way, much damage can be prevented before it can begin.

Two of the more prominent system capabilities concern date aggregation and application via artificial intelligence. The system, because of its passive data collection nature, can collect and aggregate data across multiple brands and types of office equipment. Artificial Intelligence and Machine Learning Algorithms can then be applied to this encompassing data to facilitate connections among data and the profiles, and acting appropriately upon deviations, as described herein.

Figure 2:
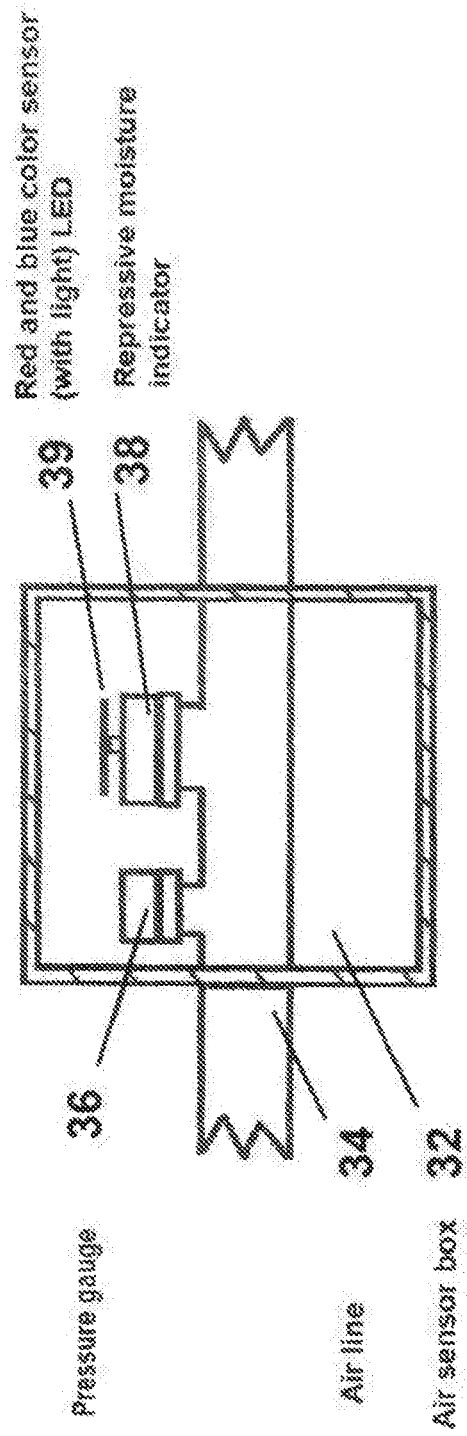
FIG. 2 is a schematic side view of a portion of the embodiment of FIG. 1, depicted in a cutaway form.

Turning to FIG. 2, the air sensor box 32 is shown in cutaway to illustrate greater detail a specific type of non-invasive sensor apparatus therein. The air sensor box 32 encapsulates sensor apparatus for monitoring the air line 34 and detecting any noticeable changes that can indicate problems. A pressure gauge 36 monitors the pressure within the line 34 and if the pressure changes, raising or lowering, outside the profile, this information can be transmitted to the main unit 12.

Next to the pressure gauge is apparatus 38, 39 for monitoring the moisture within the air line 34 and if the moisture moves past an allowable limit set in the profile, this information can likewise be transmitted to the main unit 12. In this specific embodiment, the moisture apparatus is comprised of a repressive moisture indicator 38, also known as a liquid contact indicator, and a Red & Blue, or Red-Green-Blue color (RGB)/LED sensor set with LED light ("RGB/LED Sensor set") 39. The regressive moisture indicator is a technology well-known in the art. It is comprised of paper or strips that, by design, remain a first color when dry, and turn a second color when exposed to a given amount of moisture. Typically, as here, the dry color is blue and the wet or moist color is red.

The RGB sensor portion of the RGB/LED Sensor set 39 is a relatively simple sensor designed and provided to detect a color change from blue to red or pink. The RGB sensor is capable of providing a read out of the color of a specific object in front of it. For example, and in this embodiment, the RGB/LED sensor can be placed in front of a repressive moisture indicator. Any deviation in color beyond the range that the RGB sensor is set to recognize as "good" color will be detected and result in alarm being sent by the system. The LED light on the sensor is to illuminate the indicator.

If there is a leak that raises moisture and the repressive moisture indicator turns red, the RGB sensor detects the change in color and is programmed such that an attached LED light, preferably a red light, turns on, when the color change occurs. T The LED light sensor portion reads the activation of the LED light and this information is transmitted to the main unit 12 as discussed, or elsewhere as appropriate, by wired or wireless means. Multiple sets of repressive moisture indicator 38 and RGB/LED sensor sets 39 can be placed, as appropriate, on lines and equipment throughout the dental practice.

Figure 3:
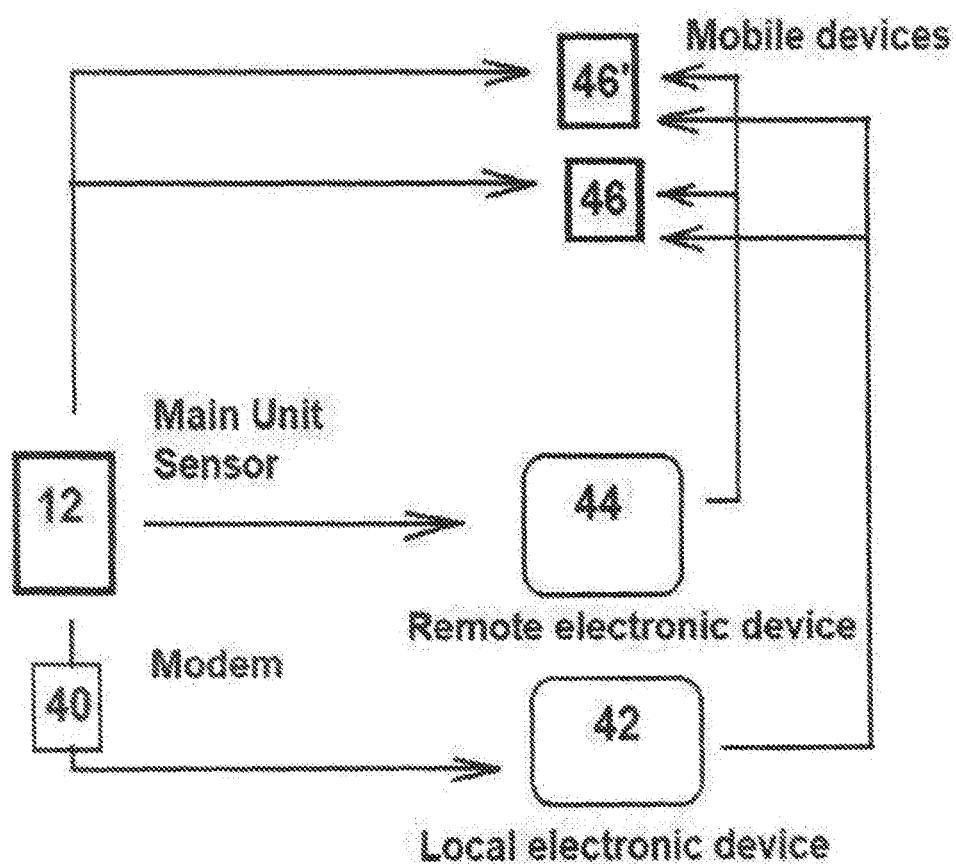
FIG. 3 is a schematic diagram showing several possible overall configurations of the data/alert notification aspect of the invention.

Turning to FIG. 3, if one or more aspects of the incoming non-invasive sensor data move outside the specific dental monitoring system profile, such as, e.g., an abnormally raised sound level of the equipment, vibration, or increased moisture content, the main unit 12 can recognize this and transmit a general or more descriptive alert, depending upon what it is programmed to do, via means known in the art. Routine data, at specified intervals, can also be transmitted.

For example, the data or alert can be sent to another local device 42 such as, e.g., a practice PC or laptop that the main unit is directly connected to, or it can be sent, as in this embodiment, as a signal via a modem 40 to the local electronic device 42. In this way, anyone with access to the local electronic device, such as a technician or call center would be notified quickly that there is a situation so that needed local action can be quickly taken.

The main unit can, alternatively, be fitted with software and components such that it can transmit to a remote electronic device 44. For example, the unit microprocessor can be capable of accessing the internet and sending data to a server or cloud, to be forwarded to appropriate personnel. For example, a technician or monitoring company can constantly remotely monitor the data, via the link between remote device 44 and main unit 12 and receive any alerts, so they can move pro-actively to deal with any concerning changes in conditions. The main unit may also be fitted with software and components making it capable of sending routine data or an alert to a mobile device or devices 46, 16' such as a smart phone or tablet, such that anyone that should be notified can be notified in real or nearly real time. The local device 42 or remote device 44 can also be provided with the capability of forwarding data or alerts to the mobile devices.

In any event, an alerted party or parties, which can be someone who works for the practice, a technician or service contracted to that practice, or other party, can receive the notification and check the equipment immediately. This can result in the detection of problems before they grow and replacement or repair of equipment before it breaks down, increasing practice efficiency and avoiding extra costs.

In one embodiment, suitable remote monitoring apparatus is provided at a suitable location, such as at a maintenance company monitoring station or call center. This notification system allows either the dental practice to conveniently request a technician for repair or request another service or product be sent to the practice, and/or the monitoring station or call center to proactively find issues and send technicians to provide repair of maintenance before the dental practice needs to. This also allows the monitoring center or call station, either by dental practice request on its own initiative, to send appropriate labels and instructions for the practice to conveniently send a piece of equipment away for maintenance or repair. A remote or on-site display can also show the dental practice's maintenance history and schedule, including technician visits and activity, as help locate relevant invoices.

Aggregated or collected data and/or alerts based upon such data, can be presented to any suitable pre-determined parties in a number of ways known in the art. This can include texts or alerts to smartphones, other electronic messaging, or via the internet, which may be in the form of, for example, an email. SMS, or Push Notifications. Further, a notification or data app may be used in conjunction with suitable electronic devices. It can also be pre-determined which parties receive which types of information and my what means. For example, during working hours, transmitting to a local electronic device may be preferred, while transmitting to a mobile device or more 44 may be preferred after work hours. Further, routine maintenance data may be transmitted to a designated technician for tracking, while an emergency flooding or fire alert can go out to every associated party to the dental office for immediate action by whoever can arrive first or call emergency personnel.

Turning to FIGS. 4-9, a number of configurations for the inventive concept are shown. As will be shown, the non-invasive dental monitoring system 10 can monitor a number of types and configurations of equipment. Some features are omitted from some respective figures for focus on more relevant features and clarity.

Figure 4:
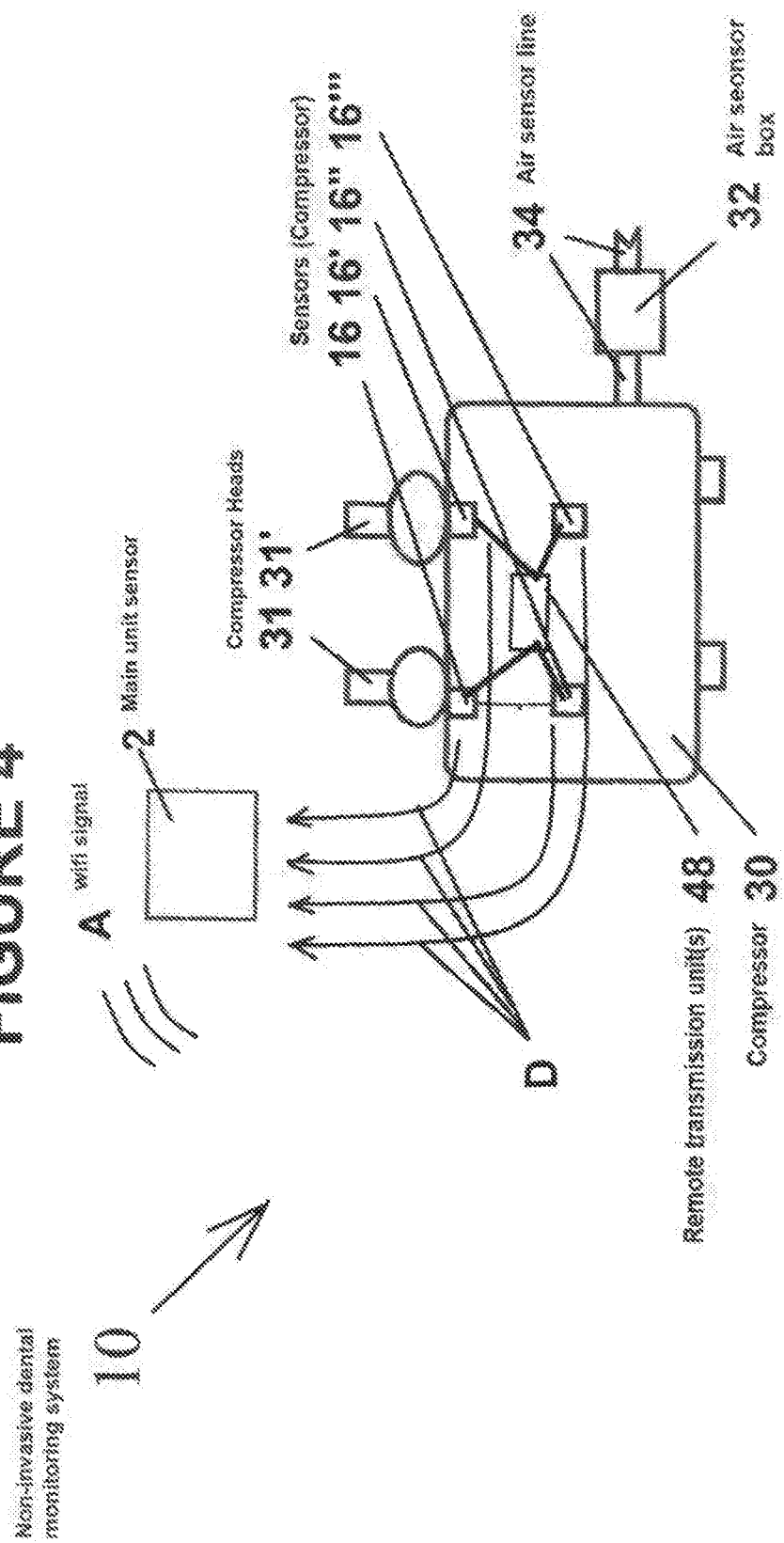
FIG. 4 is a schematic view of another embodiment of the invention with an alternative sample configuration.

Turning to FIG. 4, a first alternative embodiment is shown. The non-invasive dental monitoring system 10 is shown used with a dual head compression system with wet ring vacuum. Professional applications such as dental practices often require a compressor that can provide increased air pressure to increase the volume of vacuum. Here, a single compressor 30 is used with dual 31, 31' or multiple heads run in parallel to increase the volume. The compressor 30 in this embodiment has dual heads 31, 31' and the compressor and heads are monitored by the system via sensors fitted about the compressor 16, 16' 16". 16'''.

Any sensor or sensors, particularly those located outside the equipment room, can have a wireless signaling device 48 wired to or built into the sensors, that is capable of transmitting data from the sensors 16, 16',16",16''' to the main unit 12 for processing, just as with a wired transmission. An example of wireless transmission is shown in this embodiment, but can apply to any suitable embodiment or configuration. In this embodiment, the sample set of sensors depicted are those of the compressor 18, 16',16",16'''. Data input is collected by the wireless signaling device 48, which in turn transmits wireless signals to the main unit 12, as indicated by arrow D, sharing information about the status of their respective devices as would be the case for a wired system. The signals D are transmitted to the main unit 12 and processed as other received data from the sensors 16, 16',16",16'''. The wireless signaling device 48 can be in a small box along with the needed sensors, or the sensors 16, 16',16",16''', may be more spread out from the wireless device. The connection between the wireless transmission device 48 and sensors 16, 16',16",16''' can also be wireless or wired. If remote power is required for the wireless transmission device 48 (for example if a power supply is not immediately handy), this can be included. The main unit 12 can be powered by any suitable means including, as in this embodiment, an AC/DC transformer.

Figure 5:
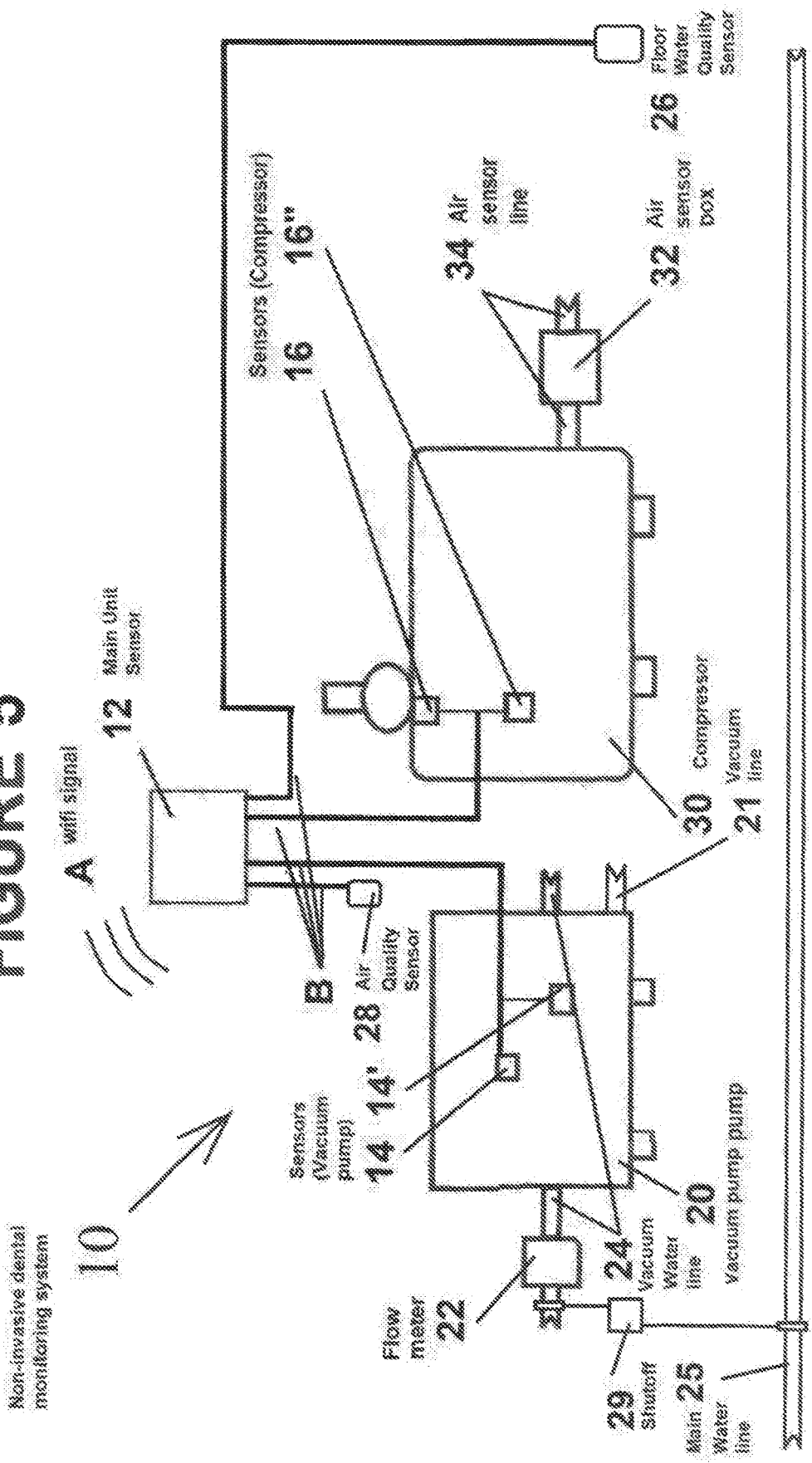
FIG. 5 is a schematic view of yet another embodiment of the invention with an alternative sample configuration.

Turning to FIG. 5, another alternative embodiment is shown. A configuration of the non-invasive dental monitoring system 10 is shown wherein the compressor 30 is a single head type with a single vacuum pump 20. In this case, the vacuum pump 20 is a wet ring vacuum pump: a vacuum pump in which an operating liquid is put into motion, often by an impeller, and accelerated, forming a liquid ring.

Figure 6:
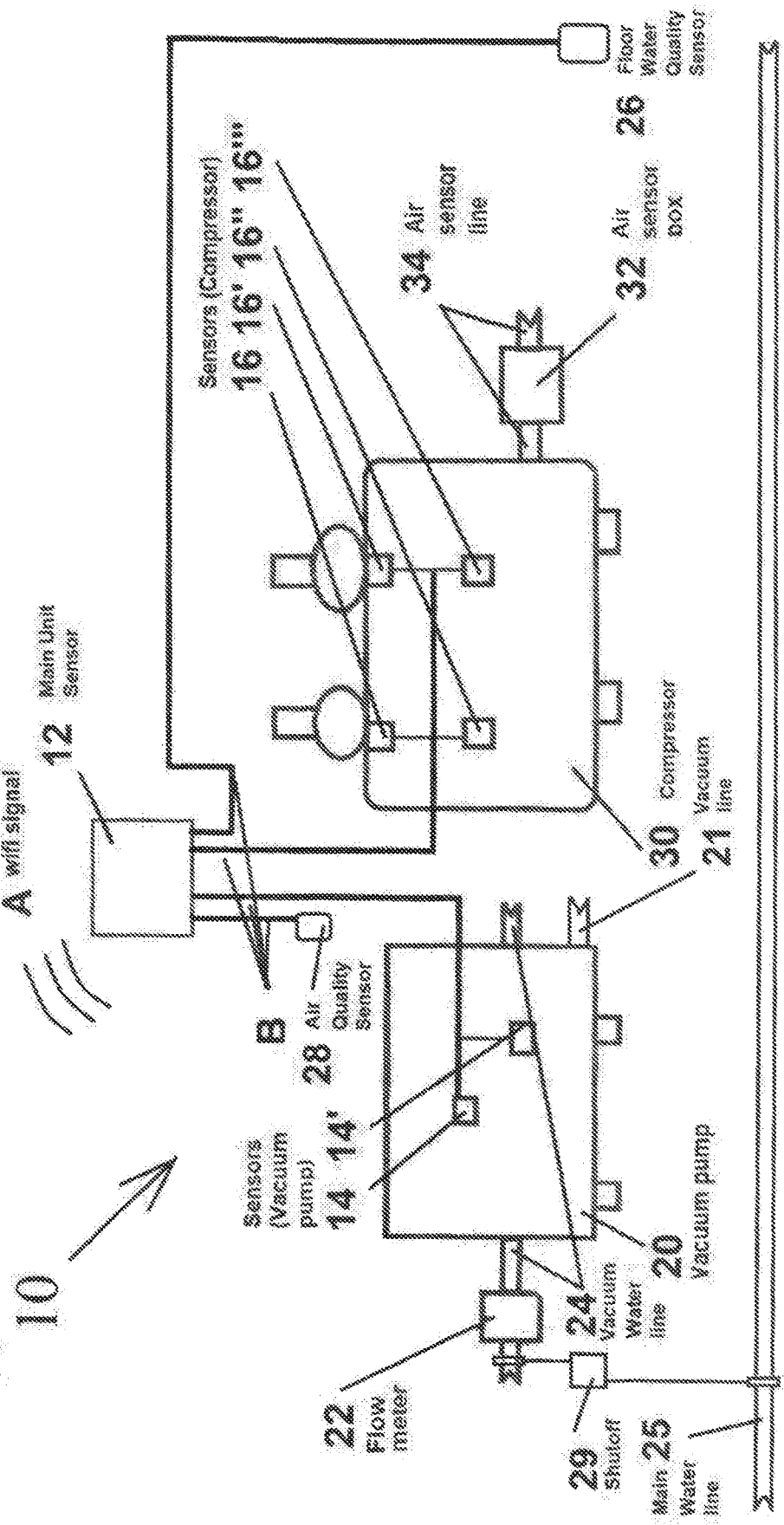
FIG. 6 is a schematic view of yet another embodiment of the invention with an alternative sample configuration.

Turning to FIG. 6, another alternative embodiment is shown. A configuration of the non-invasive dental monitoring system 10 is shown wherein the compressor 30 is a dual head compressor and a vacuum pump 20. The vacuum pump can be of any suitable type, such as a regular pump, a wet ring vacuum pump or as in this embodiment, a two-state pump such as, e.g., a dual pump wet ring vacuum pump. A dual stage wet ring vacuum pump is a type of pump in which the discharge from the first stage discharges through a manifold leading to a second stage through a discharge port between first- and second-stage impellers, and the second stage allows a deeper vacuum.

Figure 7:
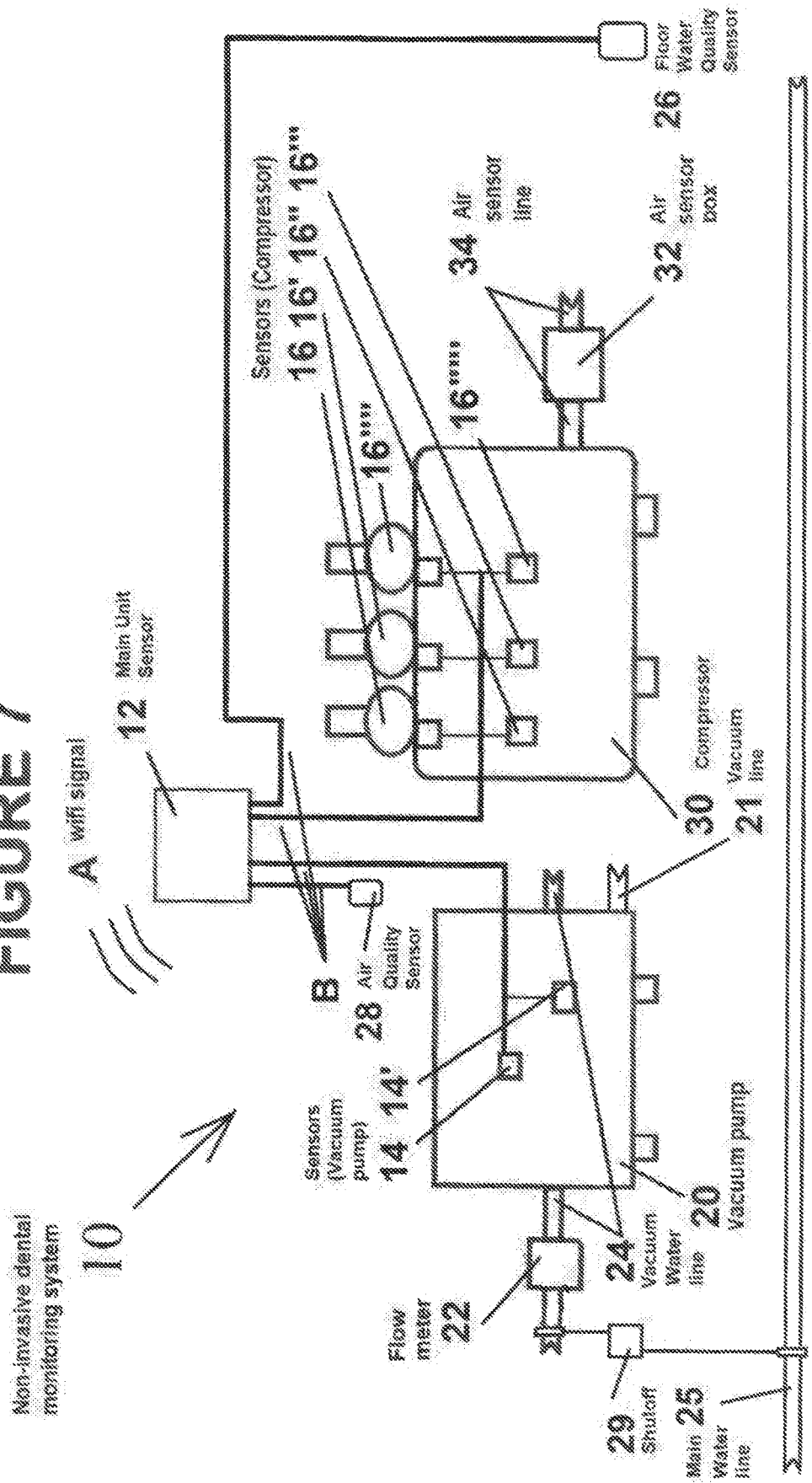
FIG. 7 is a schematic view of yet another embodiment of the invention with an alternative sample configuration.

Turning to FIG. 7, another alternative configuration embodiment is shown. An embodiment of the non-invasive dental monitoring system 10 is shown, wherein the compressor 30 is a triple head compressor, with a triple set of compressor sensors 16, 16',16",16''', 16'''', 16''''' and the vacuum pump 20 is a dual pump dry type vacuum.

Figure 8:
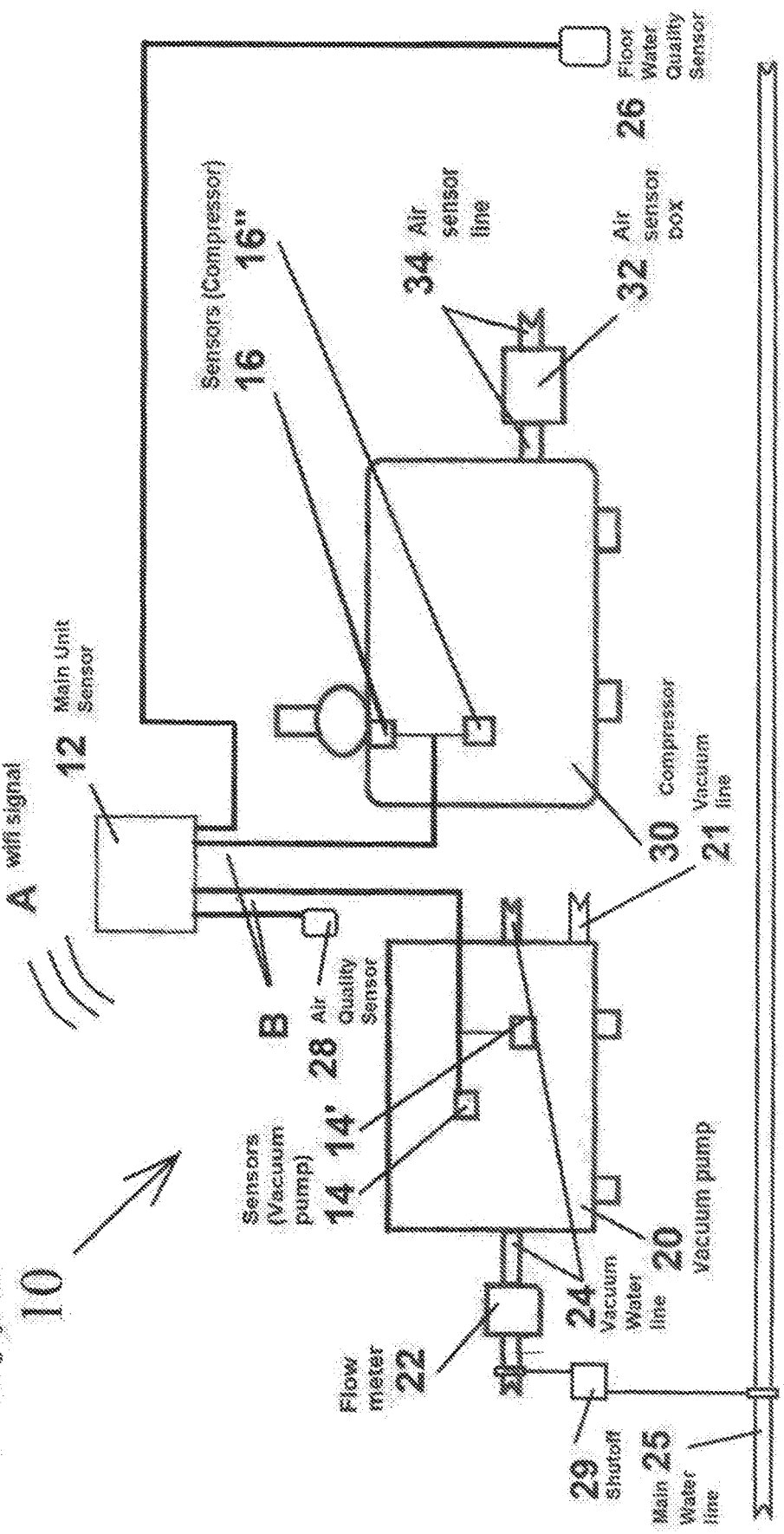
FIG. 8 is a schematic view of yet another embodiment of the invention with an alternative sample configuration.
Figure 9:
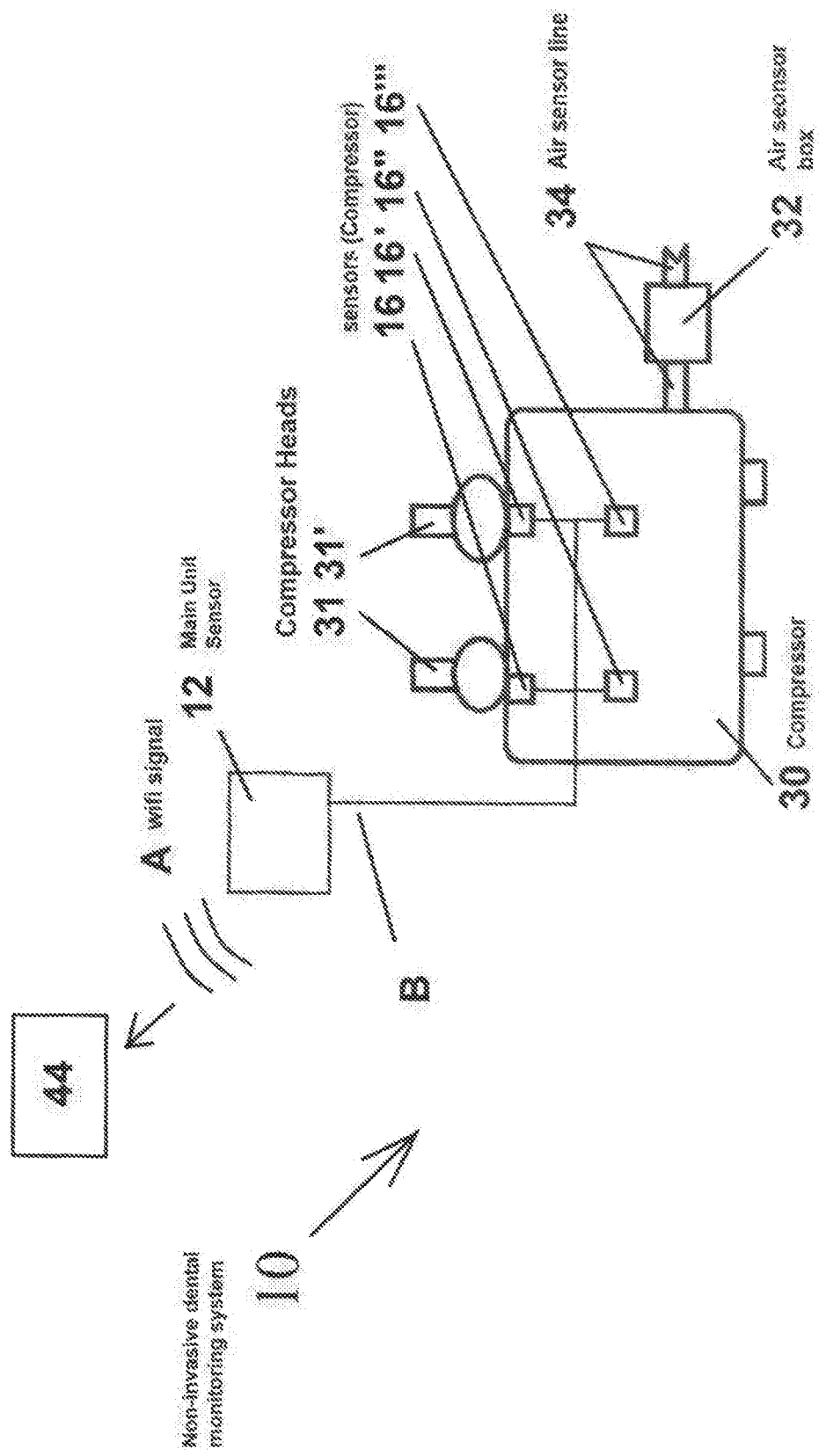
FIG. 9 is a schematic view of yet another embodiment of the invention with an alternative sample configuration.

Turning to FIG. 8, another configuration of the non-invasive dental monitoring system 10 is shown, wherein the compressor 30 is a single head compressor and the vacuum pump is with single pump dry vacuum Turning to FIG. 9, and returning briefly to FIG. 3, another configuration of the non-invasive dental monitoring system 10 is shown, wherein the equipment to be monitored is a compressor 30, and the compressor 30 is a dual head compressor. Also in this embodiment, the sensors 16, 16', 16",16''' are sending data to a remote display at the portable electronic device 44 via the main sensor unit 12 so that the compressor 30 can be monitored from any location.

Figure 10:
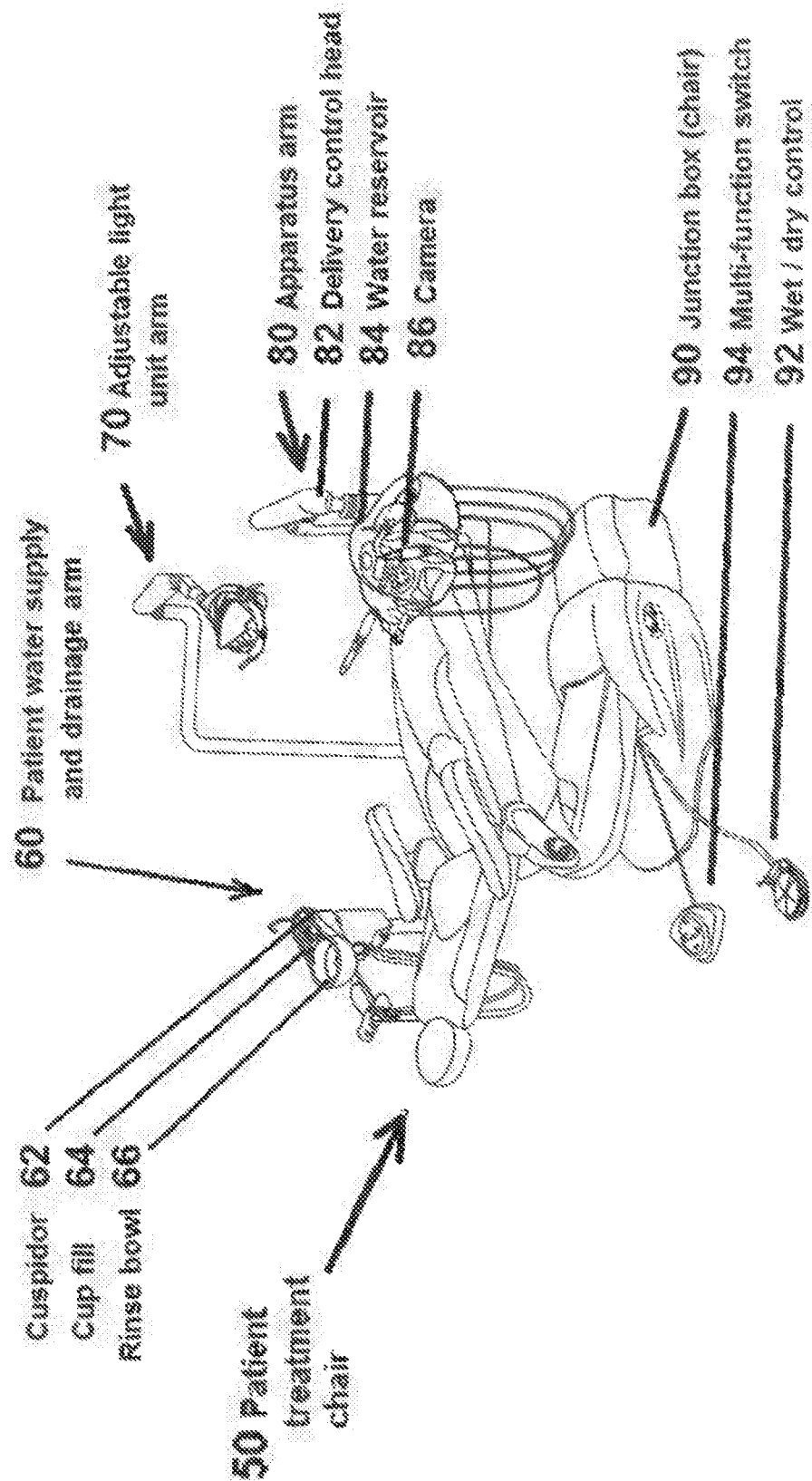
FIG. 10 is a perspective view of showing an embodiment of the delivery portion of the system.

Turning to FIG. 10, an embodiment of the monitoring system 10 including delivery end of patient services is shown. A patient treatment chair 50 is shown. The patient treatment chair 50 shown has some equipment features typical to a dental practice, and as will be shown, a number of new features related to the invention herein. The patient treatment chair 50 includes, generally, a patient water supply and drainage arm 60, an adjustable light unit arm 70, an and apparatus arm 80.

The adjustable light unit arm 70 has appropriate lighting and movable arm(s) to provide light where needed to conduct dental work. The patient water supply and drainage arm 60 includes some water-related apparatus for dentistry. The apparatus include a cuspidor 62 for draining water away from the patient as needed, a cup fill 64 for supplying a patient with water, and a rinse bowl 66 for supplying initial rinse.

The apparatus arm 80 includes a number of features, including a water reservoir and delivery control head 82. The delivery control head 82 controls a number of dental devices as known in the art and may be useful for patient care. These may include, for example, a suction tube operated via vacuum for moisture drainage, mirror, tools for blowing air, drills, polishers, picks, and the like.

Referring briefly back to FIG. 1 as well as FIG. 10, the doctor or other professional can use each delivery head 82 to drive some or all of their instruments. The delivery control head 82 is typically used to drive the final stage of water delivery and circulation. This is typically done via connection of the deliver control head 82 to the vacuum pump 20 and compressed air delivery via connection to the compressor 30 to operate pneumatic equipment such as the drills and polishers.

The delivery control head 82, as in this embodiment, is typically located at or near point of contact with the patient, and can be, as in this embodiment, part of the dental or surgical chair, adjacent to the chair, or as will be shown, other suitable nearby location, such as, above or below in a cabinet or shelf.

The patient treatment chair 50 is further comprised of controls to operate the chair by the dentist or other preferred party. In this embodiment, these include a wet/dry control 92 for controlling water flow, and a multi-function switch 94 for controlling other functions. In this embodiment, these controls are foot-controlled, though they can be of any suitable configuration in the art.

The patient treatment chair further has a Junction box (chair) 90, which will be discussed in more specific detail during the upcoming description of FIG. 12.

The junction box 90 plays an important role in monitoring and regulating the patient treatment chair 50 and its water, air, and vacuum related features, as well as water pressure, air pressure, and vacuum strength The junction box 90, as will be discussed, can have regulators for water, air and vacuum flow and respective sensors which can act separately from the regulators or as dual units. Further, the control units 92, 94 for controlling at least some of the dental apparatus of the chair can have sensors in addition to, or alternative to, any within the junction box for monitoring levels or activity of air, water, or vacuum and making appropriate adjustments or alerts.

Further, a camera 86, video, snapshot, or a combination of these activities, can be present and running as an information collection source for, example, collecting video of a patient's teeth for study, or documenting a surgery or other treatment. The camera can be located in any suitable location, and in this embodiment, is located as part of the delivery head 82. The dental camera 86 can be of any type known in the art for enhancing patient care, such as, for example, a Sopro™ type camera.

Figure 11:
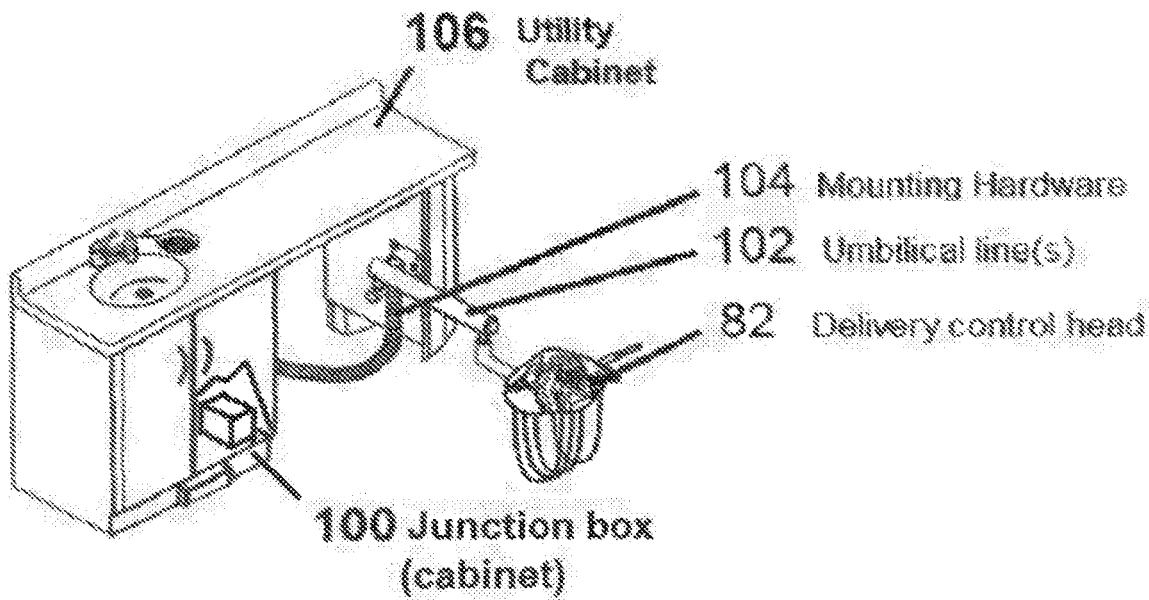
FIG. 11 is a perspective view, in partial cutaway, showing an embodiment of a portion of the equipment of the inventive system.
Figure 11A:
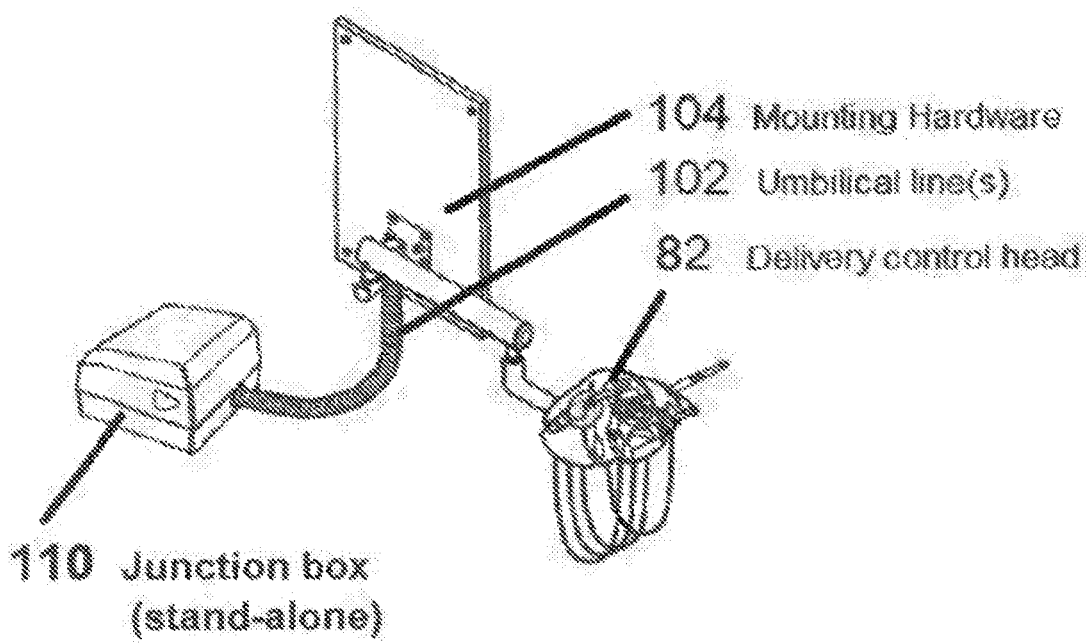
FIG. 11A is a perspective view showing an alternative embodiment of a portion of the equipment of the inventive system.

Turning generally to FIGS. 11 and 11a, the monitoring and regulating equipment of the treatment area can be of any suitable location and configuration. These can be in multiple locations, though greater efficiency may be achieved by placing these in a single location, as in the embodiments herein. In the embodiments of FIGS. 10-11a, this equipment is located in a single junction box for efficiency and ease of maintenance and use. As shown by the embodiments of these figures, different types of junction boxes, with differing configurations and locations, may be used, based upon factors including, for a few examples, amount of space, type of patient chair used, area configuration, and other individual circumstances.

Turning specifically to FIG. 11, in an additional embodiment, a junction box (cabinet) 100 is located in a utility cabinet 106, and the junction box 100 is shown in a partial cutaway. The utility cabinet 106 can be in the shape of an upright cabinet of shelves, sink counter (as in this embodiment) or other suitable configuration. In this embodiment, air, water and vacuum lines run into the utility cabinet 106. These lines can run, in whole or in part, past or through the junction box 100 via an umbilical line or lines 102. In this embodiment, all of these lines are incorporated into a single umbilical line 102. Mounting hardware 104 provides support to the delivery head 82, and the lines within the umbilical line 102 can run via the mounting and support hardware 104 to the delivery head 82, which is typically mounted on a flexible arm.

Any mounting or support hardware 104, delivery head 82, junction box 100 and lines 102 can be in any suitable configuration for providing the functions described herein. This is an arrangement wherein the delivery head 82 and regulating and sensor equipment is located at or within the cabinet 106 for easy storage and use.

Turning to FIG. 11A, other locations and arrangements for the delivery control head and related equipment are possible. In this embodiment, the delivery unit is mounted on a nearby wall, with the umbilical line 102 leading to a more visible junction box in the form of a stand-alone junction box 110.

Figure 12:
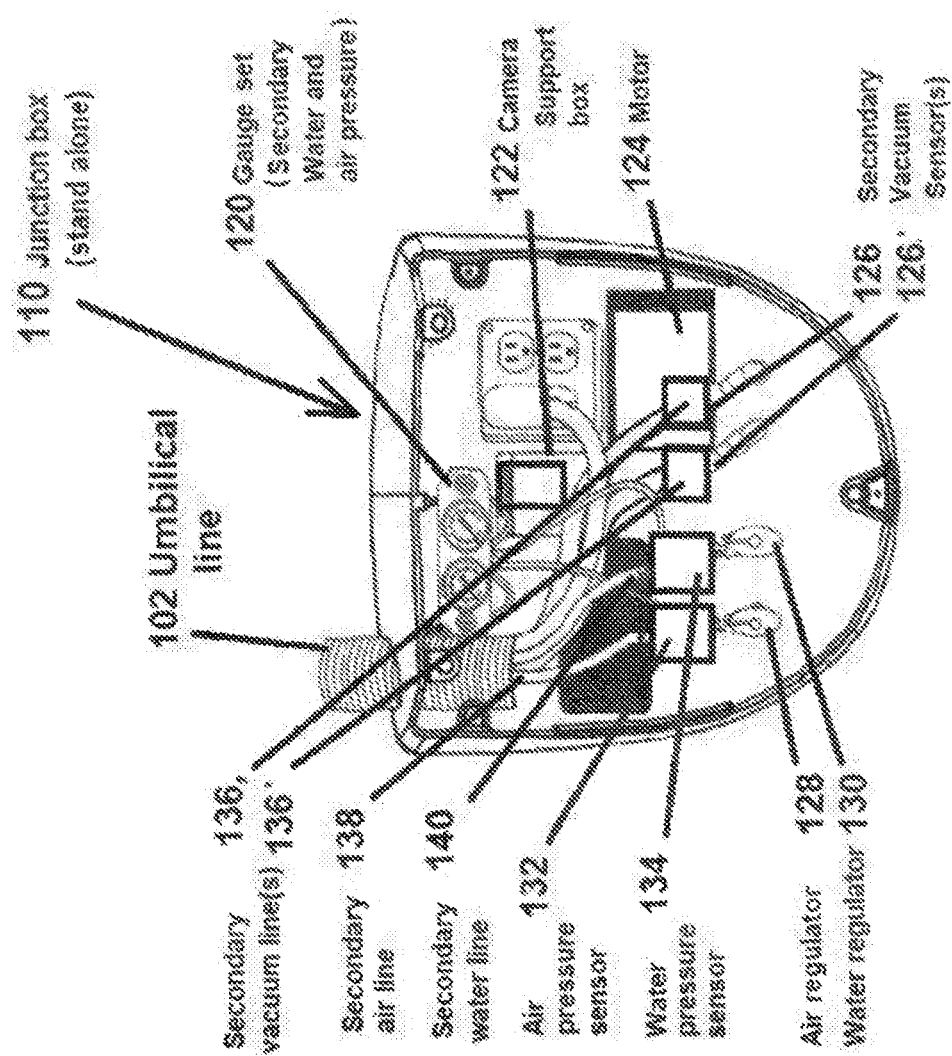
FIG. 12 is a perspective view, in full cutaway, further focusing on an specific portion of the equipment of the embodiments of FIGS. 10-11A.

Turning to FIG. 12, the junction box, and secondary monitoring and regulating equipment, will be discussed in greater detail. In FIG. 12, a configuration of the junction box 110 of FIG. 11 is shown, though this discussion applies to other junction boxes herein as well.

The junction box 110 can include, among other components of the system, pressure gauges for visibly showing system conditions, sensors for important information like air, water and vacuum pressure, splice points for connecting gauges to sensors, and regulators to maintain control of any or all of these conditions. In this embodiment, the junction box 110 is in a small plastic box with tubes coming out of the junction box for splicing into existing service lines like air, water and vacuum. In this way, the junction box 110 can be set up to help provide monitoring of the dental equipment without actively interfering with any of its operation.

In an opened view of the junction box 110, the umbilical line 102 enters the junction box 110. Once in the junction box 110, the lines within the umbilical line 102 go to their respective locations and apparatus.

In this embodiment, one or more secondary vacuum lines (represented herein as 136, 136*a*), one or more secondary air line(s) (represented herein as 138), and at least one secondary water line (represented herein as 140) are depicted.

There may be advantages to having connected primary and secondary lines. The primary water and air lines 24, 34, for example, can be, as in this embodiment, in a utility room or other area with machinery like the main vacuum pumps) 20 or compressor(s) 30. In this area, the lines can be of a harder, sturdier material for easier maintenance such as PVC or other plastic, steel, or stainless steel. As the lines move into the treatment area, it can become advantageous to be able to easily manipulate the lines, and have material that can more easily be branched and spliced about, and attach the lines within the junction box 110 and within a number of device connection points within the delivery control head.

To accomplish these objectives, the primary lines, such as the primary water line 24 and primary air line 34 may be designed to flow directly to the junction box, or as in this embodiment, flow to, and be in communication with, a secondary water line 138 or secondary water line 140. These secondary lines may be of a thinner, more flexible or malleable material that enable them to be more easily placed and manipulated within the junction box 110 and spliced and attached to a number of instruments on the delivery control head 82.

In this embodiment, the secondary vacuum lines 136, 136', secondary air line 138, and secondary water line 140 extend outward from the umbilical 102 along their respective paths to the devices of the delivery control head 82, or to other suitable devices in other suitable locations. These lines can have the types of sensors as previously discussed here, and regulator apparatus.

At least one secondary air pressure sensor(s) 132 is attached to the secondary air line 138, and can monitor air-related factors, as discussed herein, including, for example, pressure, temperature, and composition, as discussed previously herein.

An air regulator 128 capable of providing needed alteration of air pressure flow can also be attached along the at least one air line 138. The air regulator 128 can also provide changes, in pressure. In some cases, the pressure of air provided by an air pump can be different, often higher, than the pressure needed to operate equipment. For example, a number of air pumps maintain air pressure of 100-120 psi, which is positive for successful flow, but a number of end user devices need an operating pressure of about 80 psi. The air regulator 128 can bring the pump pressure down to that needed to operate the devices.

Similarly, at least one secondary water pressure sensor(s) 134 is attached to the secondary water line 138, and can monitor liquid-related factors, as discussed herein, including, for example, pressure, temperature, and flow, as discussed previously herein.

A water regulator 130 capable of providing needed alteration of air pressure flow can also be attached along the at least one water line 140. The water regulator 130 can also provide changes in pressure. In some cases, the pressure of air provided by a water pump can be different than the pressure needed to operate equipment. For example, a number of a number of end user devices need an operating pressure of about 40 psi, while water pressure can vary by location. The water regulator 130 can bring the pump pressure down to that needed to operate the devices.

The secondary vacuum lines 126, 126' can be in communication with a primary vacuum line 21 from the main vacuum pump 20. The secondary vacuum lines 126, 126*a* can have secondary vacuum sensors 136, 136' attached to the respective lines. The secondary vacuum sensors 136, 136' can monitor similar vacuum characteristics at the vacuum pump sensors 14 14', such as flow and vacuum pressure.

The secondary sensors herein, such as water, air, or vacuum, can be, as with the case of the other sensor apparatus discussed previously herein, wired or wirelessly connected to the main unit sensor 12. Data from these sensors, as with other sensors herein, can then be transmitted, monitored, and used as additional system data input as discussed herein.

Gauges or other readout apparatus can also be attached to provide an immediate indicator of important activity. In this embodiment, a set of gauges showing air and water pressure 120, connected to the secondary air and water lines 138, 140 is present The junction box 110 can also have a motor 124 or other known power source in the art such as a battery for powering any portion or all of the equipment of the delivery control head, chair, or other location.

The junction box 110 can accommodate additional equipment as well. In this embodiment, a dental camera control box 122 is powered by, and located at, the junction box and includes an appropriate array of video ports for supporting the camera 86.

The delivery control head 82 or other pieces of equipment can also have any appropriate sensors for providing needed data on associated equipment. For example, the delivery control head 82 might have an air pressure sensor to detect if a problem has occurred with the delivery system and the drive air pressure has elevated or decreased to a point that the equipment will not operate correctly, could potentially become damaged, or could potentially injure a patient. As another example, the delivery control head 82 may also have a vacuum sensor to monitor vacuum strength throughout the day and detect potential blockages in the vacuum system.

Additionally, there can be a remote unit at or near the chair to combine data from the delivery equipment and/or chair, process the data at that point, and send summary or conclusory data back to the main unit 12. In other words, this unit may act as a remote or satellite unit to the main unit 12, processing a set of information about the delivery area and transmitting that information back.

Disclosed herein is a holistic, non-invasive system for effectively monitoring dental facilities system with minimal effort by those working at the dental facility, that can increase efficiency, prolong equipment life, and reduce equipment and patient costs.

It is to be understood that while certain forms of the present invention have been illustrated and described herein, the expression of these individual embodiments is for illustrative purposes and should not be seen as a limitation upon the scope of the invention. It is to be further understood that the invention is not to be limited to the specific forms or arrangements of parts described and shown.

DENTAL MONITORING SYSTEM COMPONENT LIST

10 Non-invasive dental monitoring system
12 Main Sensor Unit
14, 14' Sensors (Vacuum pump)
16, 16',16",16''', Sensors (Compressor)
16'''', 16'''''
17 Water Sensor
18, 18' Room sensors
19, 19' RPM Sensors
20 Vacuum pump
21 Vacuum line
22 Flow meter
24 Vacuum water line
25 Main water line
26. Floor Water Sensor in Utility Room
28. Air Quality Sensor in Utility Room'
29 Shutoff
30 Compressor
31, 31' Compressor heads
32 Air sensor box
34 Air line
36 Pressure gauge
38 Repressive moisture indicator
39 Red & Blue color sensor with light LED
40 Modem
42 Local electronic device
44 Remote electronic device
46, 46' Mobile device(s)
48 Remote transmission unit(s)
50 Patient treatment chair
60 Patient water supply and drainage arm
62 Cuspidor
64 Cup fill
66 Rinse bowl
70 Adjustable light unit arm
80 Apparatus arm
82 Delivery control head
84 Water reservoir
86 Camera
90 Junction box (chair)
92 Wet/dry control
94 Multi-function switch
100 Junction box (cabinet)
102 Umbilical line(s)
104 Mounting hardware
106 Utility cabinet
110 Junction box (stand-alone)
120 Gauge set (secondary air and water pressure)
122 Camera support box
124 Motor
126, 126' a Secondary Vacuum sensor(s)
128 Air regulator
130 Water regulator
132 Secondary air pressure sensor(s)
134 Secondary water pressure sensor(s)
126, 126' Secondary Vacuum sensor(s)
136, 136' Secondary vacuum lines
138 Secondary air line
140 Secondary water line
A Wifi Signal
B Sensor lines
C Wifi to remote device display
D Wireless signals from sensors to main sensor unit

The invention claimed is:

1. A non-invasive dental or surgical equipment monitoring system comprising:
a main sensing unit;
at least one set of sensors, including at least one sensor, configured to indirectly monitor at least one piece of dental or surgical related equipment by collecting at least one kind of indirect data regarding at least one piece of equipment indicating at least one condition of the at least one piece of equipment, wherein the at least one sensor comprises either:
at least one current transformer sensor configured to measure current flowing to electric motors,
at least one humidity sensor configured to measure ambient humidity from the piece of equipment,
at least one temperature sensor configured to measure ambient air temperature from the piece of equipment,
at least one housing temperature sensor configured to measure temperature of a housing of a motor,
at least one vibration sensor configured to detect changes in balance and vibration of at least one pump, one motor, or both,
at least one sound sensor configured to collect audio data generated from the piece of equipment,
at least one air quality detector configured to detect a level of at least one pre-determined substance in the air from the piece of equipment,
at least one air pressure sensor configured to detect air tank pressure, purge air pressure, or both,
at least one moisture sensor configured to detect changes in moisture to detect increased or decreased moisture,
at least one water flow sensor configured to monitor water flow rate within a waterline,
at least one room sensor configured to monitor general environmental condition of a dental room, surgical room, or a mechanical room,
at least one round-per-minute (RPM) sensors configured monitor an operating speed of at least one motor,
or a combination thereof,
wherein each sensor of the sensor set is removably attached to each respective at least one piece of equipment, does not have direct control of, direct interaction with, or operation of each respective at least one piece of equipment, and is not un-removably attached to or combined with each respective at least one piece of equipment,
wherein each sensor of each sensor set is either
in wired or wireless communication with the main sensing unit and is configured to send the indirect data to the main sensing unit,
or the system is further comprised of sensor data transmission equipment configured to transmit the indirect data wirelessly from each sensor to the main sensing unit,
or a combination thereof;

and at least one local electronic device or at least one remote electronic device, either wired or wirelessly connected to the main sensor unit, and configured to receive data from the main sensor unit, wherein the main sensing unit is further comprised of a processor configured to receive data from the sensor set, process the received data, and either display the data, or send the data to the at least one local electronic device, or send the date to the at least one remote electronic device, or a combination thereof.

2. A non-invasive monitoring system according to claim 1, wherein the at least one piece of dental or surgical equipment is comprised of at least one pump or compressor with at least one line protruding from the at least one pump or compressor, wherein the at least one line is a vacuum line, water line, air line, or combination thereof.

3. A non-invasive monitoring system according to claim 1, wherein at least one local or remote electronic device is a remote electronic device, and the at least one electronic device is configured to receive an alert transmitted from the main sensor unit.

4. A non-invasive monitoring system according to claim 1, further comprised of a shutoff configured to perform a function of immediately turning off portions or all of the equipment, shutting off water flow to an area, or both, wherein the shutoff configured to perform a function of being activated manually, remotely, or automatically by the system, when certain pre-determined emergency parameters are met.

5. A non-invasive monitoring system according to claim 1, wherein the at least one sensor of the sensor set is comprised of a moisture sensing apparatus, wherein the moisture sensing apparatus is comprised of a repressive moisture indicator configured to indicate a first color when dry and a second color when wet, at least one LED light, a red, green and blue (RGB) sensor configured to perform the function of detecting a color change from the first color to the second color and activating the at least one LED light, and at least one LED light sensor portion configured to detect the activation of the LED light and transmitting this information to the main sensor unit.

6. A non-invasive monitoring system according to claim 1, further comprised of at least one power source configured to perform a function of powering the main unit, part or all of the sensor set, or both.

7. A non-invasive monitoring system according to claim 1, wherein the system is further comprised of a delivery apparatus set, comprised of:

a treatment chair, and a delivery control head, wherein the delivery control head is comprised of at least one dental or surgical device that uses vacuum, water, air, or a combination of the above to function, wherein the delivery control head is connected to at least one secondary line that is connected, directly or indirectly, to at least one vacuum pump at least one water line, at least one air compressor, or a combination thereof, Le and a power source for the treatment chair, delivery control head, or both.

8. A non-invasive monitoring system according to claim 7, wherein the at least one dental or surgical device of the delivery control head is comprised of at least one sensor within the delivery control head to perform a function of monitoring at least one dental or surgical device within the delivery control head.

9. A non-invasive monitoring system according to claim 7, wherein the delivery control head is further comprised of a remote unit configured to perform a function of combining data from at least one sensor within the delivery control head, the treatment chair, a junction box, or a combination thereof, processing the data, and sending summary or conclusory data back to the main sensor unit.

10. A non-invasive monitoring system according to claim 1, further comprising a junction box, and at least one secondary line, wherein the at least one secondary line is at least one vacuum line, air line, water line, or some combination thereof, and is connected to a primary, wherein the junction box is comprised of secondary monitoring and regulating equipment, wherein the secondary monitoring and regulating equipment is comprised of at least one secondary sensor configured to perform a function of collecting data about vacuum, air or water, or a combination thereof of each respective at least one secondary line, at least one air regulator, water regulator, or combination thereof, attached to at least one secondary line.

11. A non-invasive monitoring system according to claim 10, further comprised of at least one readout apparatus attached to at least one secondary line and configured to perform a function of providing an immediate indicator of activity, or at least one camera for collecting visual treatment data, or at least one control unit configured to perform a function of controlling at least some of the apparatus of the treatment chair, or a combination thereof.

12. A method for non-invasively monitoring a dental or surgical practice comprised of:

providing a main sensing unit, providing at least one set of sensors, comprised of at least one sensor configured to indirectly monitor at least one piece of dental or surgical related equipment by collecting at least one kind of indirect data regarding the at least one piece of equipment indicating the condition of the at least one piece of equipment, wherein the at least one sensor comprises either:

at least one current transformer sensor configured to measure current flowing to electric motors, at least one humidity sensor configured to measure ambient humidity from the piece of equipment, at least one temperature sensor configured to measure ambient air temperature from the piece of equipment, at least one housing temperature sensor configured to measure temperature of a housing of a motor, at least one vibration sensor configured to detect changes in balance and vibration of at least one pump, one motor, or both, at least one sound sensor configured to collect audio data generated from the piece of equipment, at least one air quality detector configured to detect a level of at least one pre-determined substance in the air from the piece of equipment, at least one air pressure sensor configured to detect air tank pressure, purge air pressure, or both, at least one moisture sensor configured to detect changes in moisture to detect increased or decreased moisture,
at least one water flow sensor configured to monitor water flow rate within a waterline,
at least one room sensor configured to monitor general environmental condition of a dental room, surgical room, or a mechanical room,
at least one round-per-minute (RPM) sensors configured monitor an operating speed of at least one motor,
or a combination thereof,
wherein each sensor of the sensor set is removably attached to each respective at least one piece of equipment, does not have direct control of, direct interaction with, or operation of each respective at least one piece of equipment, and is not un-removably attached to or combined with each respective at least one piece of equipment,
wherein each sensor of each sensor set is either
in wired or wireless communication with the main sensing unit and is configured to send the indirect data to the main sensing unit,
or the system is further comprised of sensor data transmission equipment configured to transmit the indirect data wirelessly from each sensor to the main sensing unit,
or a combination thereof;
removably attaching each sensor of the sensor set to each respective at least one piece of equipment,
wherein each sensor does not have direct control or interaction over the operation of each respective at least one piece of equipment,
and is not un-removably attached to or combined with each respective at least one piece of equipment
either:
placing each sensor of each sensor set in wired communication with the main sensing unit such that each sensor is configured to send the indirect data to the main sensing unit,
or providing sensor data transmission equipment configured to transmit the indirect data wirelessly from each sensor to the main sensing unit,
or a combination thereof,
providing:
at least one local electronic device connected to the main sensor unit directly or wirelessly,
or at least one remote electronic device configured to receive transmissions from the main sensor unit,
providing apparatus configured to receive data from the sensor set, sending the data to
the at least one local electronic device,
the at least one remote electronic device,
or a combination thereof,
and providing at least one processor configured to process the indirect data.

13. A method for non-invasively monitoring a dental or surgical practice according to claim 12, further comprising:
collecting the indirect data from the sensor set,
processing the data for a pre-determined period of time,
creating a profile of sensor data based upon the processed data,
using the profile to set a baseline behavior pattern of data based on the profile,
setting or receiving a specified acceptable range of data behavior based on the baseline behavior pattern,
monitoring incoming sensor data to determine whether any of the at least one piece of equipment is operating out of the specified range, and
sending a notification or alert if the sensor data indicates any of the at least one piece of equipment is operating out of the specified data range.

14. A method for non-invasively monitoring a dental or surgical practice according to claim 1, comprising the further steps of:
collecting the indirect data from the sensor set,
applying machine learning, predictive analysis, or other type of artificial intelligence algorithm or algorithms to process and analyze the data to discover patterns of behavior of the at least one piece of dental or surgical equipment over a period of time,
to create a profile of baseline behavior of the at least one piece of dental or surgical equipment,
finding potential or current equipment problems by spotting a deviation from the baseline profile, and
reacting in or calculated or pre-programmed manner to a deviation from the baseline profile.

15. A method for non-invasively monitoring a dental or surgical practice according to claim 14, further comprising the step of reacting by sending a notification or alert to at least one pre-designated party via at least one electronic device.

16. A method for non-invasively monitoring a dental or surgical practice according to claim 12, comprising the further steps of: providing at least two denial or surgical practices, comparing and aggregating the data of a similar piece of equipment of the at least two practices, using the aggregated date to determine an average or standard signature for the piece of equipment.

17. A method for non-invasively monitoring a dental or surgical practice according to claim 12, comprising the further steps of:
providing a pre-determined remote device for monitoring the transmitted data from the main sensor unit,
presenting the collected data, the baseline profile, alerts or notifications when there is a deviation from the baseline profile to the monitoring device.

\* \* \* \* \*